(12) United States Patent
Ding et al.

(10) Patent No.: US 8,673,183 B2
(45) Date of Patent: Mar. 18, 2014

(54) TETRAZINE MONOMERS AND COPOLYMERS FOR USE IN ORGANIC ELECTRONIC DEVICES

(75) Inventors: Jianfu Ding, Ottawa (CA); Zhao Li, Orleans (CA); Naiheng Song, Kirkland (CA)

(73) Assignee: National Research Council of Canada, Ottawa, Ontario ( * ) Notice: Subject to any disclaimer, the term of this patent is extended or adjusted under 35 U.S.C. 154(b) by 321 days.

(21) Appl. No.: 13/169,436

(22) Filed: Jun. 27, 2011

(65) Prior Publication Data

US 2012/0007026 A1    Jan. 12, 2012

Related U.S. Application Data

(60) Provisional application No. 61/361,637, filed on Jul. 6, 2010.

(51) Int. Cl.
*H01B 1/12* (2006.01)
*H01L 35/24* (2006.01)

(52) U.S. Cl.
USPC ............................. 252/500; 528/377; 136/252

(58) Field of Classification Search
USPC .................. 252/500; 528/373–377; 544/179; 549/59; 136/252
See application file for complete search history.

(56) References Cited

U.S. PATENT DOCUMENTS

| | | | |
|---|---|---|---|
| 6,991,749 B2 * | 1/2006 | Marks et al. ................. | 252/500 |
| 7,217,824 B2 | 5/2007 | Zhang et al. | |
| 7,235,320 B2 | 6/2007 | Calundann et al. | |
| 7,256,921 B2 | 8/2007 | Kumar et al. | |
| 7,286,275 B2 | 10/2007 | Kumar et al. | |
| 7,332,530 B2 | 2/2008 | Kiefer et al. | |
| 7,349,137 B2 | 3/2008 | Kumar et al. | |
| 7,349,138 B2 | 3/2008 | Kumar et al. | |
| 7,359,104 B2 | 4/2008 | Kumar et al. | |
| 7,384,552 B2 | 6/2008 | Calundann et al. | |
| 7,394,585 B2 | 7/2008 | Kumar et al. | |
| 7,429,105 B2 | 9/2008 | Kumar et al. | |
| 7,457,025 B2 | 11/2008 | Kumar et al. | |
| 7,466,469 B2 | 12/2008 | Kumar et al. | |
| 7,471,436 B2 | 12/2008 | Kumar et al. | |
| 7,683,229 B2 | 3/2010 | Stoessel et al. | |
| 7,767,777 B2 | 8/2010 | Buesing et al. | |
| 2003/0080324 A1 * | 5/2003 | Marks et al. ................. | 252/500 |
| 2007/0185303 A1 | 8/2007 | Stoessel et al. | |
| 2008/0220285 A1 | 9/2008 | Vestweber et al. | |
| 2008/0299293 A1 | 12/2008 | Sheina et al. | |
| 2009/0173378 A1 | 7/2009 | Burn et al. | |
| 2009/0184313 A1 | 7/2009 | Buesing et al. | |
| 2010/0084640 A1 | 4/2010 | Ie et al. | |
| 2010/0110362 A1 | 5/2010 | Parri et al. | |
| 2010/0163103 A1 | 7/2010 | Wang et al. | |
| 2010/0187505 A1 | 7/2010 | Stoessel et al. | |

FOREIGN PATENT DOCUMENTS

| | | |
|---|---|---|
| EP | 0261733 | 9/1987 |
| EP | 2072557 | 6/2009 |
| WO | 02/059121 | 8/2002 |
| WO | 2008/018982 | 2/2008 |
| WO | 2010/008672 | 1/2010 |
| WO | 2010/022058 | 2/2010 |
| WO | 2010/075421 | 7/2010 |

OTHER PUBLICATIONS

Abdel-Rahman MO, Kira MA, Tolba MN. (1968) A Direct Synthesis of Dihydrotetrazine. Tetrahedron Letters. 35, 3871-3872.
Abdelwahed R. Sayed, 1,3-Dipolar cycloaddition polymerization reactions of novel macromolecules containing sym-tetrazine rings, Polymer 49 (2008) 2253-2259.
Asawapirom U, Scherf U. (2001) Dialkylcyclopentadithiophene Polymers and Copolymers. Macromol. Rapid Commun. 22, 746-749.
Audebert P, Sadki S, Miomandre F, Clavier G. (2004a) First example of an electroactive polymer issued from an oligothiophene substituted tetrazine. Electrochemistry Communications. 6, 144-147.
Audebert P, Sadki S, Miomandre F, Clavier G, Vernieres MC, Saoud M, Hapiot P. (2004b) New J. Chem. 28, 387.
Audebert P. (2006a) J. Phys. Chem. A. 110, 12971-12975.
Audebert P. (2006b) Chem. Commun. 3612-3614.
Audebert P. (2009a) J. Electroanal. Chem. 632, 201-205.

Audebert P. (2009b) Eur. J. Org. Chem. 6121-6128.

Chen L-M, Hong Z, Li G, Yang Y. (2009a) Recent Progress in Polymer Solar Cells: Manipulation of Polymer: Fullerene Morphology and the Formation of Efficient Inverted Polymer Solar Cells. Adv. Mater. 21, 1434-1449.

Chen H-Y, Hou J, Zhang S, Liang Y, Yang G, Yang Y, Yu L, Wu Y, Li G. (2009b) Polymer solar cells with enhanced open-circuit voltage and efficiency. Nature photonics. 3, 649-653.

Cheng Y-J, Yang S-H, Hsu C-S. (2009) Synthesis of Conjugated Polymers for Organic Solar Cell Applications. Chem. Rev. 109, 5868-5923.

Clavier G, Audebert P. (2010) s-Tetrazines as Building Blocks for New Functional Molecules and Molecular Materials. Chem. Rev. 110, 3299-3314.

Coffin RC, Peet J, Rogers J, Bazan GC. (2009) Streamlined microwave-assisted preparation of narrow-bandgap conjugated polymers for high performance bulk heterojunction solar cells. Nature Chemistry. 1, 657.

Coppo P, Cupertino DC, Yeates SG, Turner ML. (2003) Synthetic Routes to Solution-Processable Polycyclopentadithiophenes. Macromolecules. 36, 2705-2711.

Dennler G, Scharber MC, Brabec CJ. (2009) Polymer-Fullerene Bulk-Heterojunction Solar Cells. Adv. Mater. 21, 1323-1338.

Dumas-Verdes C, Miomandre F, Lépicier E, Galangau O, Vu TT, Clavier G, Méallet-Renault R, Audebert P. (2010) BODIPY-Tetrazine Multichromophoric Derivatives. Eur. J. Org. Chem., 113, 2525-2535.

Forrest Sr. (2004) Nature. 428, 911.

Günes S, Neugebauer H, Sariciftci NS. (2007) Conjugated Polymer-Based Organic Solar Cells. Chem. Rev. 107, 1324-1338.

Halls JJM, Walsh CA, Greenham NC, Marseglia EA, Friend RH, Moratti SC, Holmes AB. (1995) Nature. 376, 498-500.

Hou J, Chen H-Y, Zhang S, Chen RI, Yang Y, Wu Y, Li G. (2009) Synthesis of a Low Band Gap Polymer and Its Application in Highly Efficient Polymer Solar Cells. J. Am. Chem. Soc. 131, 15586-15587.

Hoven CV, Dang X-D, Coffin RC, Peet J, Nguyen T-Q, Bazan GC. (2010) Improved Performance of Polymer Bulk Heterojunction Solar Cells Through the Reduction of Phase Separation via Solvent Additives. Adv. Mater. 22, E1-E4, adma.200903677.

Janowska, Izabela et al., Donor-Acceptor-Donor Tetrazines Containing a Ferrocene Unit: Synthesis, Electrochemical and Spectroscopic Properties, J. Phys. Chem. A 2006, 110, 12971-12975.

Jung IH, Jung YK, Lee J, Park J-H, Woo HY, Lee J-I, Chu HY, Shim H-K. (2008) Journal of Polymer Science: Part A: Polymer Chemistry. 46, 7148-7161.

Kaim W. (2002) The coordination chemistry of 1,2,4,5-tetrazines. Coordination Chemistry Reviews. 230 (2002) 127-139.

Kim, Yuna, et al., Tetrazine-based electrofluorochromic windows: Modulation of the fluorescence through applied potential, Journal of Electroanalytical Chemistry 632 (2009) 201-205.

Lee JK, Ma WL, Brabec CJ, Yuen J, Moon JS, Kim JY, Lee K, Bazan GC, Heeger AJ. (2008) Processing Additives for Improved Efficiency from Bulk Heterojunction Solar Cells. J. Am. Chem. Soc. 130, 3619-3623.

Li G, Shrotriya V, Yao Y, Huang J, Yang Y. (2007) J. Mater. Chem. 17, 3126.

Liang Y, Feng D, Wu Y, Tsai S-T, Li G, Ray C, Yu L. (2009a) Highly Efficient Solar Cell Polymers Developed via Fine-Tuning of Structural and Electronic Properties. J. Am. Chem. Soc. 131, 7792-7799.

Liang F, Lu J, Ding J, Movileanu R, Tao Y. (Liang 2009b) Design and Synthesis of Alternating Regioregular Oligothiophenes/Benzothiadiazole Copolymers for Organic Solar Cells. Macromolecules. 42, 6107-6114.

Liang Y, Xu Z, Xia J, Tsai S-T, Wu Y, Li G, Ray C, Yu L. (2010). For the Bright Future—Bulk Heterojunction Polymer Solar Cells with Power Conversion Efficiency of 7.4%. Adv. Mater. 22, E135-E138.

Ma W, Yang C, Heeger AJ. (2005) Adv. Funct. Mater. 15, 1617.

Mayer AC, Scully SR, Hardin BE, Rowell MW, McGehee MD. (2007) Polymer-based solar cells. Material Today. 10(11), 28-33.

Miyaura N, Suzuki A. (1995) Palladium-Catalyzed Cross-Coupling Reactions of Organoboron Compounds. Chem. Rev. 95(7), 2457-2483.

Mühlbacher D, Scharber M, Morana M, Zhu Z, Waller D, Gaudiana R, Brabec CJ. (2006) High Photovoltaic Performance of a Low-Bandgap Polymer. Adv. Mater. 18, 2884-2889.

Palmas P, et. al. (2007) Magn. Reson. Chem. 45, 65-71.

Park SH, Roy A, Beaupré S, Cho S, Coates N, Moon JS, Moses D, Leclerc M, Lee K, Heeger AJ. (2009) Bulk heterojunction solar cells with internal quantum efficiency approaching 100%. Nature photonics. 3, 297-303.

Pasquinet E, et. al. (2007) Tetrahedron. 63, 11189-11194.

Peet J, Kim JY, Coates NE, Ma WL, Moses D, Heeger AJ, Bazan GC. (2007) Efficiency enhancement in low-bandgap polymer solar cells by processing with alkane dithiols. Nature Materials. 6, 497.

Sagot E, Le Roux A, Soulivet C, Pasquinet E, Poullain D, Girard E, Palmas P. (2007) Synthesis of linear and hyperbranched tetrazine-based polyhetarylene assemblies with high nitrogen content. Tetrahedron. 63 (2007) 11189-11194.

Saracoglu N. (2007) Recent advances and applications in 1,2,4,5-tetrazine Chemistry. Tetrahedron. 63, 4199-4236.

Sayed AR, Wiggins JS. (2008) 1,3-Dipolar cycloaddition polymerization reactions of novel macromolecules containing sym-tetrazine rings. Polymer. 49 (2008) 2253-2259.

Scharber MC, Mühlbacher D, Koppe M, Denk P, Waldauf C, Heeger AJ, Brabec CJ. (2006) Design Rules for Donors in Bulk-Heterojunction Solar Cells—Towards 10% Energy-Conversion Efficiency. Adv. Mater. 18, 789-794.

Soci C, Hwang I-W, Moses D, Zhu Z, Waller D, Gaudiana R, Brabec CJ, Heeger AJ. (2007) Adv. Funct. Mater. 17, 632-636.

Soloducho J, Doskocz J, Cabaj J, Roszak S. (2003) Practical synthesis of bis-substituted tetrazines with two pendant 2-pyrrolyl or 2-thienyl groups, precursors of new conjugated polymers. Tetrahedron. 59, 4761-4766.

Stille JK. (1986) Angew. Chem. Int. Ed. 25, 508-524.

Tang CW. (1986) Appl. Phys. Lett. 48, 183-184.

Thompson BC, (2005), Variable band gap poly(3,4-alkylenedioxythiophene)-based polymers for photovoltaic and electrochromic applications, vol. 6606B of Dissertations Abstracts International. p. 3157.

Thompson BC, Fréchet JMJ. (2008) Polymer-Fullerene Composite Solar Cells. Angew. Chem. Int. Ed. 47, 58-77.

Topp K-D, Grote M. (1996) Synthesis and characterization of a 1,2,4,5-tetrazine-modified ion-exchange resin. Reactive & Functional Polymers. 3(1), 117-136.

Wang E-C. Lin G-J. (1998) A New One Pot Method for the Conversion of Aldehydes into Nitriles Using Hydroxyamine and Phthalic Anhydride. Tetrahedron Lett. 39, 4047-4050.

Wiggins JS, et. al. (2008) Polymer. 49, 2253-2259.

Yu G, Heeger AJ. (1995) J. Appl. Phys. 78, 4510-4515.

Zhu Z, Waller D, Gaudiana R, Morana M, Mühlbacher D, Scharber M, Brabec C. (2007) Panchromatic Conjugated Polymers Containing Alternating Donor/Acceptor Units for Photovoltaic Applications. Macromolecules. 40, 1981-1986.

* cited by examiner

*Primary Examiner* — Mark Kopec
(74) *Attorney, Agent, or Firm* — Laura Catherine Eckenswiller

(57) ABSTRACT

Copolymers of formula (I):

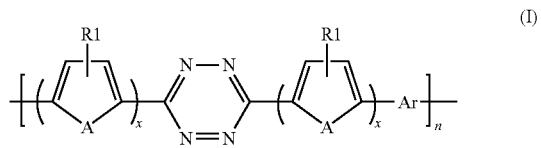

where each A is S, Se or C=C; each x is an integer from 1 to 4; each R1 is independently H, F, CN or a $C_1$-$C_{20}$ linear or branched aliphatic group; Ar is one or more substituted or unsubstituted aromatic units; and, n is an integer 5 or greater, can be formed into films or membranes that are useful as active layers in organic electronic device, such as PV solar cells, providing high power conversion efficiencies and good thermal stability. Such copolymers may be synthesized from monomers of formula (II):

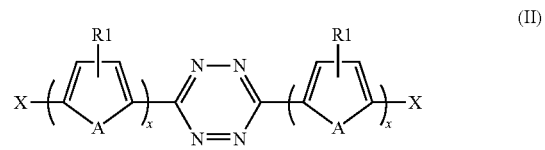

by Stille or Suzuki coupling reactions. Such monomers may be synthesized by a variation of the Pinner synthesis.

20 Claims, 8 Drawing Sheets

PTSiTTz-2,6;2,6, Poly[2,6-(4,4-bis(ethylhexyl)-dithieno[3,2-b:2',3'-d]silole)-alt-5,5'-(3',6'-bis(4-ethylhexylthien-2-yl)-s-tetrazine)]

PFTTz-8;6, Poly[2,7-(9,9-dioctylfluorene)-alt-5,5'-(3,6-bis(4-hexylthien-2-yl)-s-tetrazine)]

PBDTTTz-4,8;6, Poly[4,8-bis(3-butyloctyl)-benzo[1,2-b:4,5-b]dithiophene-2,6-alt-5,5'-(3,6-bis(4-hexylthien-2-yl)-s-tetrazine]

TETRAZINE MONOMERS AND COPOLYMERS FOR USE IN ORGANIC ELECTRONIC DEVICES

CROSS-REFERENCE TO RELATED APPLICATIONS

This application claims the benefit of U.S. Provisional Patent Application Ser. No. 61/361,637 filed Jul. 6, 2010, the entire contents of which is herein incorporated by reference.

FIELD OF THE INVENTION

The present invention relates to tetrazine monomers, copolymers produced from such tetrazine monomers, processes for preparing copolymers comprising tetrazine monomers and to uses of the copolymers in organic electronic devices.

BACKGROUND OF THE INVENTION

Organic materials including small molecules and polymers used for electronic devices have attracted much interest due to facile preparation of the materials, low cost of substrates such as plastic films, glass and metal foils, and cost-effective processing for device fabrication. In addition, organic materials have a wide variety of properties, which can be easily adjusted by molecular structure design (Forrest 2004). Since the pioneering work of the double layer organic solar cell and the concept of a bulk heterojunction solar cell (Tang 1986; Yu 1995; Halls 1995), significant progress has been made in organic photovoltaic solar cell technology. An average increase of 1% per-year in power conversion efficiency (PCE) of organic solar cells has been achieved in the last three years.

PCE represents the efficiency of a solar cell to convert incident solar power to electric power. It can be calculated based on Eq. 1 from a current-voltage (J-V) curve:

$$PCE = I_{SC} \times V_{OC} \times FF / P_i \quad (1)$$

where $V_{CO}$ is the open circuit voltage which is the maximum voltage a device can produce under irradiation without any electric load in the external circuit, $I_{SC}$ is the short circuit current which is the maximum current a device can reach under irradiation with the electric contact of the device shorted, FF is the fill factor which is a measurement of the maximum power extraction of the device with an optimized load in the external circuit, and $P_i$ is the incident solar power. The PCE value is directly related to the shape of the J-V curve.

In recent years, the fastest developing area in this field has been bulk heterojunction polymer solar cells (PSC), in which the heterojunction active layer comprises a semiconducting polymer as the electron donor (ED) domain and a fullerene derivative as the electron acceptor (EA) domain (Cheng 2009; Dennler 2009; Chen 2009a; Thompson 2008; Günes 2007; Mayer 2007). The high PCE of this type of device is attributed to a very large heterojunction area between the donor and acceptor domains. In this device, a photon is absorbed in the active layer and converted to an exciton, or an electron-hole pair. It is separated at the donor/acceptor interface to create an electron and a hole, which move along within the donor and acceptor domains to reach the relevant electrodes, respectively, to generate electricity. Therefore, the PCE of such a device is first dependent on the sunlight absorption efficiency of the polymer in the active layer. However, most semiconducting polymers absorb at a short wavelength. Up to now, the benchmark of polymer solar cell has been based on poly(3-hexylthiophene) (P3HT) as the donor and fullerene derivatives, such as PCBM, as the acceptor (see Scheme 1). Power conversion efficiencies (PCE) up to 4-5% have been reported (Ma 2005; Li 2007). However, this value already seems to be an upper limit since P3HT films only absorb light in a relative short wavelength region, having maximum absorption at about 510 nm with onset of absorption at about 630 nm, while the maximum photon flux region of the solar spectrum is about 700 nm. Thus, the majority solar energy cannot be used in these devices. Another drawback of P3HT is its high lying highest occupied molecular orbital (HOMO) energy levels at −4.9 eV. This limits the open-circuit voltage ($V_{OC}$) to around 0.6 eV because $V_{OC}$ is closely related to the difference between the HOMO energy level of the donor and the lowest unoccupied molecular orbital (LUMO) energy level of the acceptor (Scharber 2006).

Scheme 1 - Structure of P3HT and PCBM.

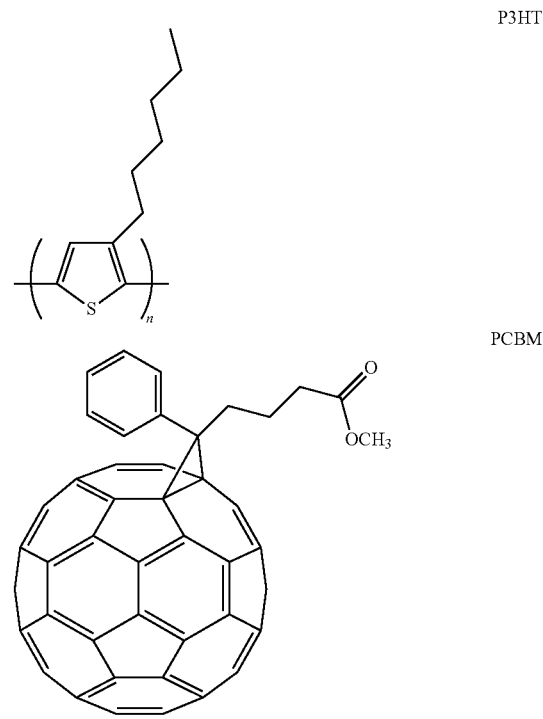

To overcome these problems, structure design of the polymer appears the most promising approach. Diverse organic chemistry benefits polymer design and synthesis, thus both the polymer structure and resulting properties can be effectively tuned. Introduction of alternating electron rich and electron deficient units into a conjugated polymer chain has proved to be an efficient way of reducing the band gap of the polymer due to electron delocalization, which results in a shift of light absorption of the polymer to longer wavelengths. By combining this with shorter wavelength absorption of the electron acceptor (e.g. fullerene derivatives), the bulk heterojunction active layer formed from the donor and acceptor can better cover the solar spectrum. In addition, the introduction of electron deficient units into the polymer also lowers LUMO and HOMO energy levels resulting in an increase in $V_{OC}$ of the device. Devices with PCE of over 6% have been reported recently by using this structure design strategy (Park 2009; Liang 2010; Liang 2009a; Chen 2009b; Hou 2009; Zhu 2007; Coffin 2009; Hoven 2010; Mühlbacher 2006; Soci 2007; Lee 2008; Peet 2007).

The cyclopenta[2,1-b:3,4-b']dithiophene (CPDT) unit has shown strong electron donating properties in conjugated polymers, and the synthesis of solution processable polycyclopentadithiophene has been reported (Coppo 2003; Asawapirom 2001). An electron rich CPDT unit alternating with an electron deficient unit in a polymer effectively narrows the band gap of the polymer, which results in very promising properties in organic electronic devices fabricated from the polymer, especially in polymer solar cells (Zhu 2007; Coffin 2009; Hoven 2010). Recently, CPDT was copolymerized with electron deficient benzothiadiazole and the resulting poly[2,6-(4,4)-bis-(2-ethylhexyl)-4H-cyclopenta[2,1-b;3,4-b']dithiophene-alt-4,7-(2,1,3-benzothiadiazole)] (PCPDTBT) shows a promising PCE of 3.5% (Mühlbacher 2006; Soci 2007). This PCE was further improved to 5% by the use of processing additives (Lee 2008; Peet 2007). However, the $V_{OC}$ of these devices was only about 0.6 V, which limits the PCEs of the devices.

Tetrazine has a very high electron affinity and it should behave as a strong electron acceptor reducing the energy level of the HOMO of polymers containing a tetrazine unit (Clavier 2010; Saracoglu 2007; Kaim 2002). Several new heterocyclic substituted tetrazines have been reported recently (Soloducho 2003; Audebert 2004a; Audebert 2004b; Audebert 2006a; Audebert 2006b; Audebert 2009a; Audebert 2009b; Dumas-Verdes 2010), and one of them (bis[5-(2,2'-bithienyl)]-s-tetrazine (see Scheme 2) was electrochemically polymerized (Audebert 2004a). The obtained copolymer showed a significantly reduced band gap and a lower LUMO level (about 0.9 eV lower than thiophene homopolymer), indicating that the tetrazine unit has significant electron accepting ability. Various other tetrazine-containing copolymers are known in the art (Abdelwahed 2008; Sagot 2007; Topp 1996), but no solution processable tetrazine-based copolymer has ever been reported.

Scheme 2 - Bis(2,2'-bithien-5-yl)-s-tetrazine

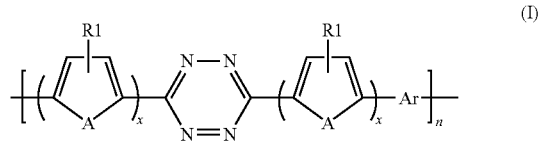

There still remains a need for tetrazine-containing copolymers that possess suitable properties for use in organic electronic devices, and for monomers and processes useful in the production of such copolymers.

SUMMARY OF THE INVENTION

In one aspect of the invention, there is provided a copolymer of formula (I):

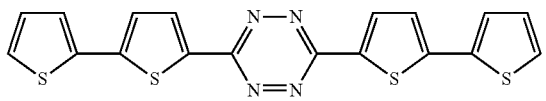

where each A is S, Se or C=C; each x is an integer from 1 to 4; each R1 is independently H, F, CN or a $C_1$-$C_{20}$ linear or branched aliphatic group; Ar is one or more substituted or unsubstituted aromatic units; and, n is an integer 10 or greater.

In another aspect of the invention there is provided a compound of formula (II):

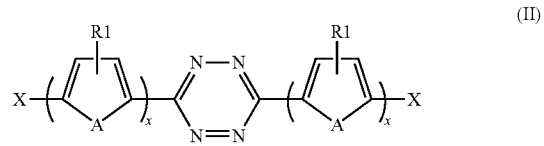

where A, X, x and R1 are as defined for the copolymer of formula (I) and each X is Br or I.

In another aspect of the invention, there is provided a process for producing a compound of formula (II):

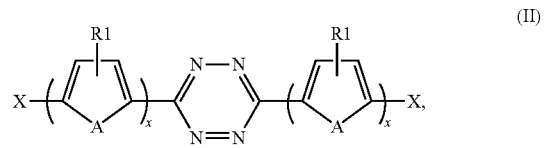

the process comprising: reacting a compound of formula (VI) with hydrazine followed by oxidation to form a compound of formula (IV):

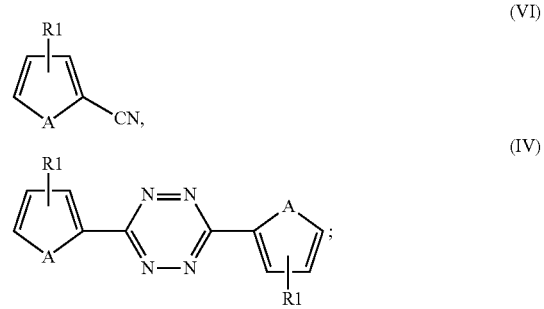

halogenating the compound of formula (IV) to form the compound of formula (II) where x is 1; and, to produce a compound of formula (II) where x is 2, 3 or 4, subsequently extending the compound of formula (II) where x is 1 by one two or three successive reactions with a compound of formula (III) in presence of a catalyst, each successive reaction with the compound of formula (III) being followed by halogenation:

where A, X, x and R1 are as defined for the compound of formula (II).

In another aspect, there is provided a film or membrane comprising a copolymer of formula (I).

In another aspect of the invention, there is provided a use of a copolymer of formula (I) as an active layer in an organic electronic device.

Compounds of formula (II) are useful as monomers for the formation of copolymers of formula (I). A is preferably S. X is preferably Br. Integer x is preferably 1. R1 is preferably a $C_1$-$C_{20}$ linear or branched aliphatic group, more preferably a $C_1$-$C_8$ linear or branched aliphatic group. Linear or branched aliphatic groups may be linear or branched alkyl, alkenyl or alkynyl groups, preferably linear or branched alkyl groups. Linear or branched aliphatic groups may be unsubstituted or substituted. Substituents may be any suitable moiety, for example, one or more of halo (e.g. F, Cl, Br, I), cyano, hydroxy, oxo, amino, amido, carboxy, nitro, thio, $C_1$-$C_{20}$-alkoxy, $C_2$-$C_{20}$-alkenoxy, $C_2$-$C_{20}$-alkynoxy, $C_1$-$C_{20}$-alkylamino, $C_2$-$C_{40}$-dialkylamino, $C_1$-$C_{20}$-alkamido, $C_2$-$C_{20}$-carboxy or $C_1$-$C_{20}$-carbonyl. Unsubstituted aliphatic groups are preferred. Some particularly preferred examples of R1 include hexyl and 2-ethylhexyl groups.

Integer n represents the number of repeating units of the monomers in the copolymer. Integer n is preferably in a range of from 5-10,000, more preferably 10-2,000.

Ar is a co-monomer unit in the copolymer of formula (I). Ar units have a cyclic structure comprising one or more aromatic rings. When Ar comprises more than one aromatic ring, each aromatic ring may be unfused, or fused to another of the aromatic rings. Ar may comprise any type of electron-rich or electron-deficient aromatic rings. Ar preferably comprises from 2 to 50 carbon atoms over all of the aromatic rings which comprise Ar. Ar may comprise aryl, heteroaryl or both aryl and heteroaryl rings. Aryl rings are preferably based on $C_6$-aromatic rings. Heteroaryl rings contain one or more heteroatoms, for example, N, O, S or Se, in the ring. Preferably, heteroaryl rings contain 1, 2 or 3 heteroatoms in the ring. Preferably, the heteroatom is N or S or both N and S. In non-aromatic parts of the cyclic structure and/or in side groups, Ar may comprise other heteroatoms, for example one or more of Si, S, Se, N, O, P.

The cyclic structure may be unsubstituted or substituted. Substituents may be any suitable moiety, for example, one or more of halo (e.g. F, Cl, Br, I), hydroxy, oxo, amino, amido, carboxy, nitro, thio, $C_1$-$C_{20}$-alkyl, $C_2$-$C_{20}$-alkenyl, $C_2$-$C_{20}$-alkynyl, $C_6$-$C_{20}$-aryl, $C_7$-$C_{24}$-alkaryl, $C_1$-$C_{20}$-alkoxy, $C_2$-$C_{20}$-alkenoxy, $C_2$-$C_{20}$-alkynoxy, $C_6$-$C_{20}$-aryloxy, $C_1$-$C_{20}$-alkylamino, $C_2$-$C_{40}$-dialkylamino, $C_1$-$C_{20}$-alkamido, $C_2$-$C_{20}$-carboxy or $C_1$-$C_{20}$-carbonyl. Preferably, the substituent is one or more of F, R2 or OR2, where R2 is a $C_1$-$C_{20}$ linear or branched aliphatic group. R2 may be unsubstituted or substituted as defined for R1. Unsubstituted R2 groups are preferred. R2 is preferably a $C_1$-$C_{20}$-alkyl group, for example hexyl or 2-ethylhexyl groups. Some examples of Ar units are shown in Scheme 3.

Scheme 3 - Examples of Ar units

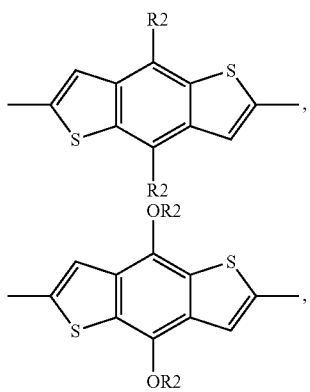

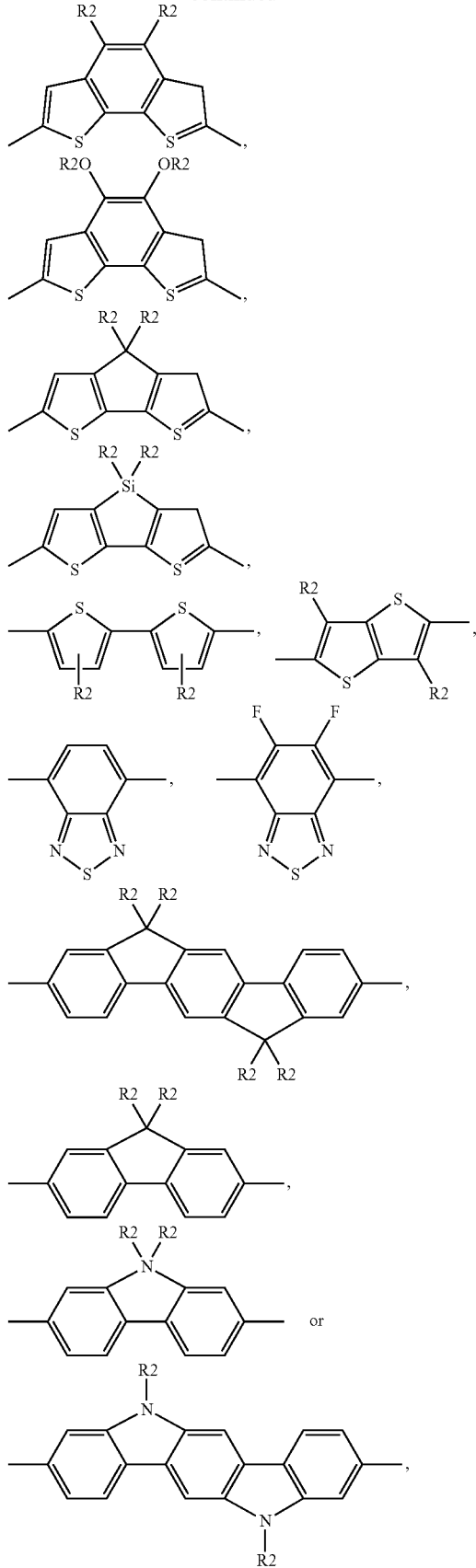

Tetrazine-containing copolymers of formula (I) are designed with an electron rich unit or another electron deficient unit, where the tetrazine unit is a very strong electron-deficient unit that efficiently reduces the HOMO and LUMO energy levels of the copolymer, while maintaining a high crystallinity level of the copolymer. These are the two most desired properties of polymers used for organic heterojunction solar cells. The copolymers exhibit good thermal stability and high power conversion efficiency (PCE). PCE of about 5% or greater, even about 5.5% or greater, are attainable. The number average molecular weight ($M_n$) of copolymers produced is typically in a range of from about 5,000 Da to about 1,000,000 Da, more specifically from about 5,000 Da to about 100,000 Da, even more specifically from about 10,000 Da to about 50,000 Da, with a relatively narrow distribution.

Copolymers of the present invention may be cast as thin films or membranes by methods generally known in the art, for example, spin-coating, casting or printing (e.g. roll printing), and ultimately assembled into organic electronic devices. The films or membranes are useful as active layers in an organic electronic device. The active layer may comprise a copolymer of the present invention as electron donor and may further comprise an electron accepting compound, for example a fullerene (e.g. phenyl $C_n$ butyric acid methyl ester (PCBM)). (6,6)-phenyl-$C_{71}$-butyric acid methyl ester is a preferred fullerene. Organic electronic devices include, for example optoelectronic devices, electroluminescence devices or field effect transistors. Such devices include, for example, optical sensors and photovoltaic devices (e.g. solar cells). Thickness of the active layer is usually in a range of from about 30 nm to about 200 nm, more preferably about 50 nm to 150 nm, depending on the light absorbance of the polymer and the charge mobility of the donor and acceptor.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
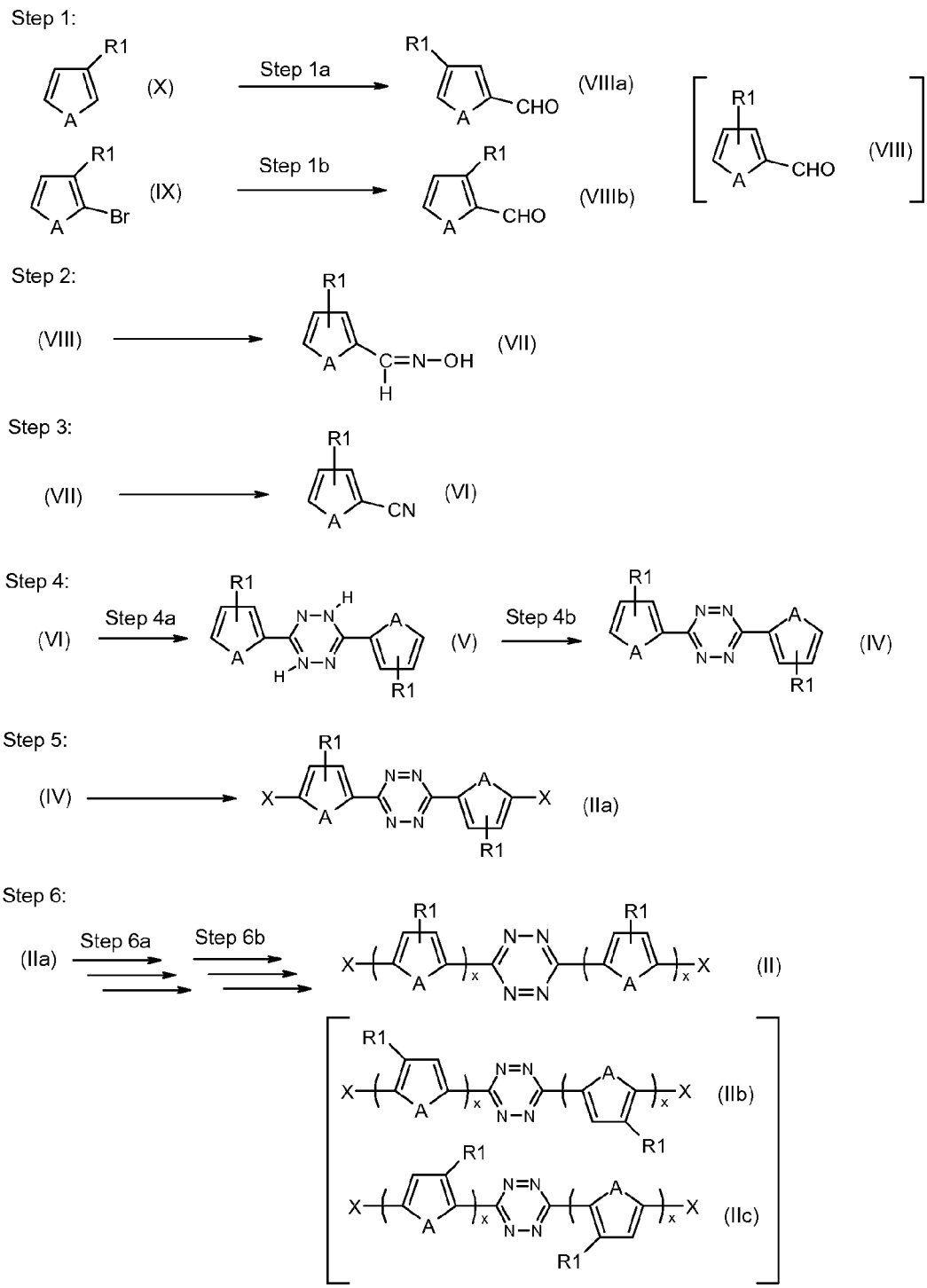
FIG. 1 depicts a reaction scheme for preparation of tetrazine-containing monomers of the present invention.

Synthesis of Monomers:

Monomers of the present invention have the general structure as defined by compound (II). FIG. 1 depicts a process for synthesizing the monomers. In FIG. 1, compound (IIa) is an embodiment of compound (II) where x is 1. Further, compound (IIb) is an embodiment of compound (II) wherein R1 is in the 4-position on the five-membered ring, while compound (IIc) is an embodiment of compound (II) wherein R1 is in the 3-position on the five-membered ring. Likewise, compounds (VIIIa) and (VIIIb) are embodiments of compound (VIII) wherein R1 is in different positions on the five-membered ring giving rise to the difference between compounds (IIb) and (IIc).

In Step 1, a 3-substituted thiophene (X) or a 2-bromo-3-substituted thiophene (IX) may be lithiated with a lithiation agent (e.g. n-BuLi) in a polar aprotic solvent (e.g. THF) and then reacted with a formyl group donor (e.g. 1-formylpiperidine or N,N-dimethylformamide) to yield the 2-formyl thiophene derivatives (VIIIa) and (VIIIb), which together may be depicted as compound (VIII) (Jung 2008).

In Step 2, the compound of formula (VIII) is reacted with hydroxylamine ($NH_2OH$), or an acid addition salt thereof, in the presence of a base (e.g. pyridine) in a protic organic solvent (e.g. ethanol) to produce oxime (VII) (Wang 1998).

In Step 3, oxime (VII) is converted to nitrile (VI) by any suitable method, for example dehydration of the oxime. Dehydration of the oxime may be conveniently effected by the use of an anhydride (e.g. acetic anhydride) in the presence of a potassium catalyst (e.g. potassium acetate) (Wang 1998).

In Step 4, a variation of the Pinner synthesis (Pinner 1893) is used in which nitrile (VI) is reacted with hydrazine (e.g. hydrazine monohydrate) to form a dihydrotetrazine intermediate (V) which is subsequently oxidized to a tetrazine (IV). Formation of the dihydrotetrazine intermediate (V) may be assisted with elemental sulfur and performed in a protic organic solvent (e.g. ethanol). It is surprising that ring closure to form the dihydrotetrazine intermediate actually works since it has been thought in the art that such dihydrotetrazine ring closure reactions would not work for substituted aryl nitriles, especially when the substituent is at the ortho-position of the aryl nitrile (Abdel-Rahman 1968). This was thought to be a result of steric effects preventing azine ring formation. Though the ring closure reaction of the nitrile with the ortho-substituent is much more difficult than the meta-substituted nitrile compound, the reaction can be done at a high temperature with the pressure regulated higher than ambient pressure, for example by using a thick wall balloon. Oxidation of the dihydrotetrazine intermediate to the fully aromatic tetrazine may be accomplished with any suitable oxidizing agent in an organic solvent (e.g. chloroform), although a nitrite, for example isoamyl nitrite, is a preferred oxidizing agent.

In Step 5, tetrazine (V) is halogenated by any suitable means to produce a dihalotetrazine (IIa), which is a compound of formula (II) in which x is 1 (Liang 2009b). Conveniently, halogenation, preferably bromination, may be effected by reacting tetrazine (V) with N-halosuccinimide, preferably N-bromosuccinimide, in a polar organic solvent (e.g. $CH_2Cl_2$) in the presence of an organic acid (e.g. acetic acid) or silica gel as a catalyst.

In Step 6, the number of 5-membered ring units in the tetrazine compound may be extended by successive reactions of the tetrazine with a 2-trimethylstannyl-substituted five-membered ring compound (III) followed by halogenation (Liang 2009b). Thus, reaction of tetrazine (IIa) with compound (III) in the presence of a catalyst (e.g. tetrakis(trimethylphosphine) palladium (0) (Pd(PPh$_3$)$_4$)) in an organic solvent (e.g. toluene, Stille 1986) followed by halogenation yields a tetrazine compound of formula (II) where x is 2. A similar subsequent reaction of the tetrazine compound of formula (II) where x is 2 with compound (III) followed by halogenation yields a tetrazine compound of formula (II) where x is 3. Yet a similar subsequent reaction of the tetrazine compound of formula (II) where x is 3 with compound (III) followed by halogenation yields a tetrazine compound of formula (II) where x is 4. Depending on whether a 3-substituted thiophene (X) or a 2-bromo-3-substituted thiophene (IX) was used in Step 1, the final product is either a tetrazine of formula (IIb) or (IIc).

Synthesis of Copolymers:

Synthetic approaches for the preparation of tetrazine copolymers of formula (I) are based on the Stille or Suzuki coupling reactions.

The Stille coupling reaction (Stille 1986):

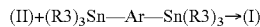
(II)+(R3)$_3$Sn—Ar—Sn(R3)$_3$→(I)

to form a copolymer of formula (I) involves the reaction of an aryl halide (a compound of formula (II)) with a stannane derivative, for example (R3)$_3$Sn—Ar—Sn(R3)$_3$, where Ar is as defined for copolymers of formula (I) and R3 is an alkyl group (e.g. methyl, ethyl, propyl, butyl). The reaction is catalyzed by a palladium(0) complex (e.g. (Pd(PPh$_3$)$_4$)) and generally performed in an organic solvent or mixture thereof (e.g. toluene, DMF).

The Suzuki coupling reaction (Miyaura 1995):

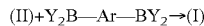
(II)+Y$_2$B—Ar—BY$_2$→(I)

to form a copolymer of formula (I) involves the reaction of an aryl halide (a compound of formula (II)) with a boronic acid derivative, for example Y$_2$B—Ar—BY$_2$, where Ar is as defined for copolymers of formula (I) and Y is OH or the two Y's taken together with their boron atom form B(OR4O) wherein R4 is an alkylene bridge (e.g. —CH$_2$CH$_2$— or —CH(CH$_3$)CH(CH$_3$)—). The reaction is catalyzed by a palladium (0) complex (e.g. (Pd(PPh$_3$)$_4$)) and generally performed in an organic solvent or mixture thereof (e.g. toluene) in the presence of an aqueous solution of a base (e.g. sodium carbonate).

Figure 2:
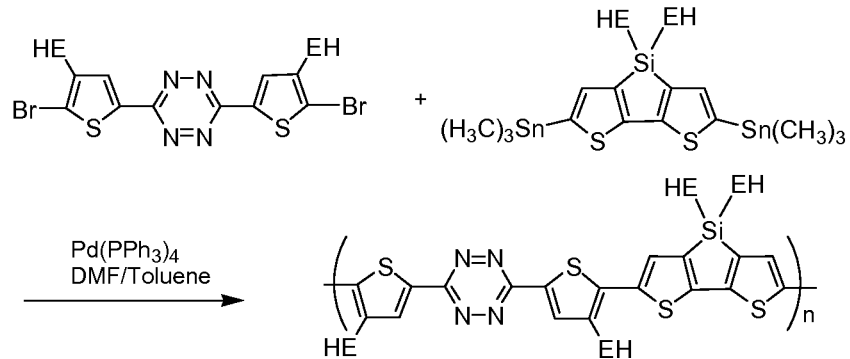
FIG. 2 depicts examples of preparation of tetrazine-containing copolymers of the present invention.
Figure 2:
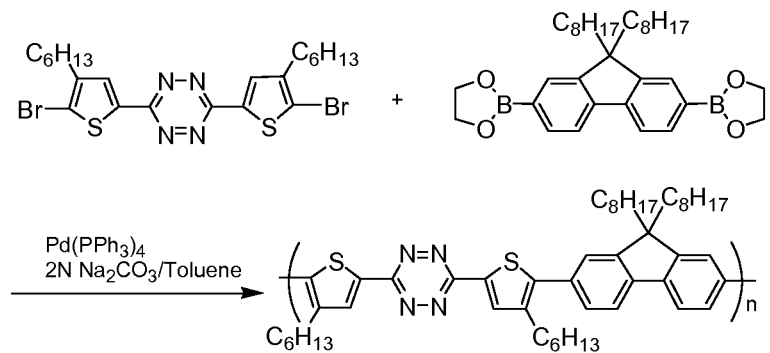
Figure 2:
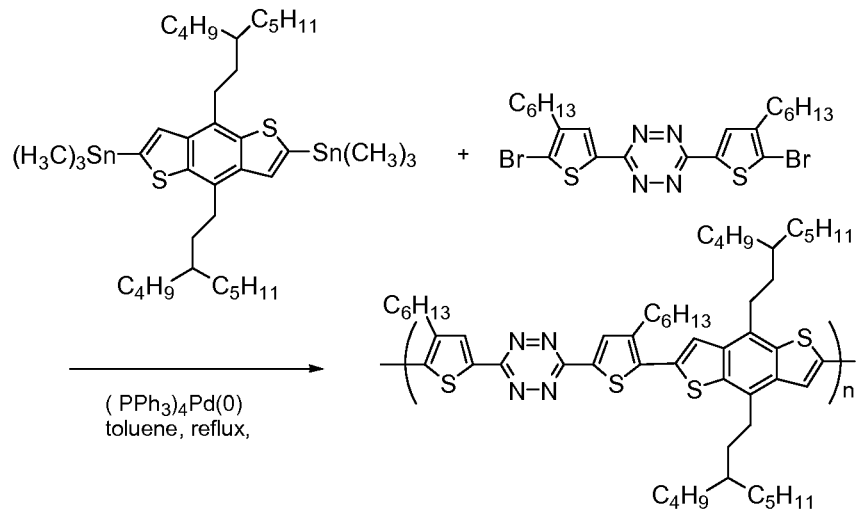

Some specific examples of the Stille and Suzuki coupling reactions are shown in FIG. 2. After the copolymers are prepared, they may be purified by any suitable method. One convenient method is Soxhlet extraction using an organic solvent, for example acetone and then hexane, followed by collection with another organic solvent, e.g. chloroform, toluene or o-dichlorobenzene (DCB). The obtained solution was concentrated and then dropped into acetone to precipitate the polymer.

Figure 3:
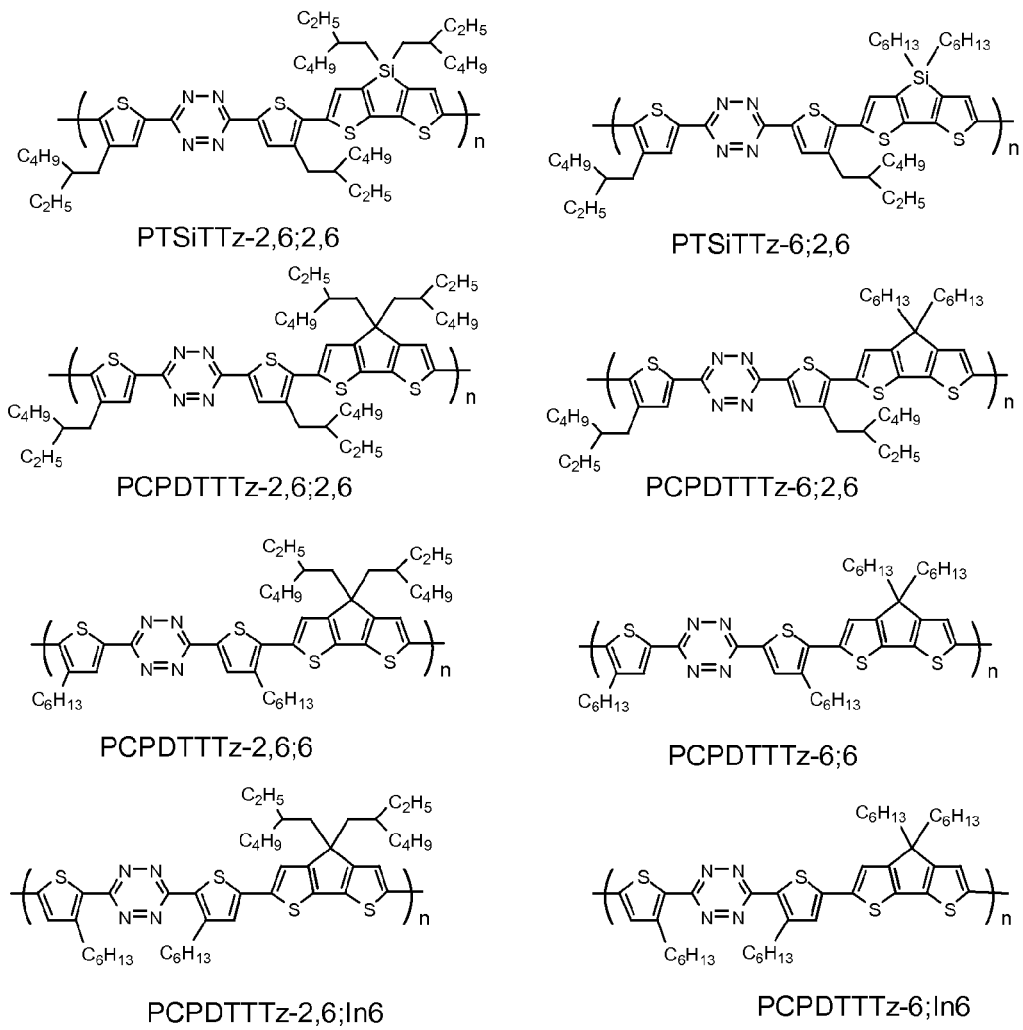
FIG. 3 depicts name and structure of selected tetrazine-containing copolymers of the present invention.

Some examples of the names and structures of copolymers of formula (I) are shown in FIG. 3. The following terminology was used for naming the copolymers: TSi and TTz represent dithieno[3,2-b:2',3'-d]silole and bisthienyl-s-tetrazine, respectively; for poly[2,6-(4,4-bis(ethylhexyl)-dithieno[3,2-b:2',3'-d]silole)-alt-5,5'-(3',6'-bis(4-ethylhexylthienyl-2-)-s-tetrazine)] (PTSiTTz-2,6;2,6), the first two digits (2,6) represent ethylhexyl side groups on the TSi unit, and the last two digits (2,6) represent ethylhexyl side groups on the TTz unit at the 4-position; when the ethylhexyl side groups were at the 3 position, the designation "In" is added ahead of the corresponding number; and, following the same rule, CPDT and TTz in the PCPDTTz series copolymers (e.g. poly[2,6-(4,4-dihexyl-4H-cyclepenta[2,1-b:3,4-b']dithiophene)-alt-5,5'-(3',6'-bis(4-hexylthienyl-2-)-s-tetrazine)]) represent 4H-cyclepenta[2,1-b:3,4-b']dithiophene and bisthienyl-s-tetrazine, respectively.

EXAMPLES

Methods

NMR spectra were recorded in CDCl$_3$, or 1,2-dichlorobenzene-d$_4$ using a Varian Unity Inova spectrometer at a resonance frequency of 399.96 MHz for $^1$H and 100.58 MHz for $^{13}$C. UV-vis spectra were measured using a Varian Cary 5000 Spectrometer. HRMS was measured with Kratos Concept 1S Mass Spectrometry.

Gel permeation chromatography (GPC) (Waters Breeze HPLC system with 1525 Binary HPLC Pump and 2414 Differential Refractometer) was used for measuring the molecular weight and polydispersity index (PDI). Chlorobenzene was used as eluent and commercial polystyrenes were used as standard.

Differential scanning calorimetry (DSC) analysis was performed under a nitrogen atmosphere (50 mL/min) using a TA Instruments DSC 2920 at a heating rate of 10° C./min, calibrated with the melting transition of indium. Thermal gravimetric analysis (TGA) was performed using a TA Instruments TGA 2950 at a heating rate of 10° C./min under a nitrogen atmosphere (60 mL/min).

Cyclic voltammetry (CV) measurements were carried out under argon in a gas-tight three-electrode cell using 0.1 M Bu$_4$NPF$_6$ in anhydrous CH$_3$CN as the supporting electrolyte. The copolymers were coated on the platinum-working electrode. The CV curves were recorded referenced to an Ag quasi-reference electrode, which was calibrated using a ferrocene/ferrocenium (Fc/Fc$^+$) redox couple (4.8 eV below the vacuum level) as an external standard. The $E_{1/2}$ of the FdFc$^+$ redox couple was found to be 0.40 V vs. the Ag quasi-reference electrode. Therefore, HOMO and LUMO energy levels of the copolymers can be estimated using the empirical equation $E_{HOMO}=-(E_{ox}^{on}+4.40)$ eV and $E_{LUMO}=-(E_{red}^{on}+4.40)$ eV, respectively, where $E_{ox}^{on}$ and $E_{red}^{on}$ stand for the onset potentials for oxidation and reduction relative to the Ag quasi-reference electrode, respectively.

Example 1

Synthesis of 3,6-bis[5-bromo-4-(2-ethylhexyl)thien-2-yl]-s-tetrazine monomer 4-(2-Ethylhexyl)-2-thiophenecarboxaldehyde 3-(2-Ethylhexyl)-thiophene (19.6 g, 100 mmol) and anhydrous tetrahydrofuran (250 mL) were charge into a 500 ml flask. The solution was cooled to −78° C. with dry ice/acetone. N-butyl lithium (40 mL, 2.5 M in hexane, 100 mmol) was dropped into the solution. After addition, the reaction solution was warmed to room temperature and stirred for 30 min. Then, the solution was cooled to −78° C. again and 1-formylpiperidine (13.6 g, 120 mmol) was added in one shot. The reaction solution was allowed to warm slowly to room temperature and stirred at room temperature for overnight. The solution was acidified with hydrochloric acid (2 N) and then extracted with ether (2×100 mL). The organic extracts were combined and washed with distilled water (2×100 mL), dried over anhydrous magnesium sulfate and rotary evaporated to remove the solvent. The residue was run through a silica-gel column using ethyl acetate/hexanes (1/10, v/v, Rf=0.3) as the eluent to give a colorless liquid product (18.4 g, 78% yield). $^1$H NMR (400 MHz, CDCl$_3$) δ (ppm): 9.86 (s, 1H), 7.56 (s, 1H), 7.34 (s, 1H), 2.59 (d, 2H, J=6.8 Hz), 1.58 (m, 1H). 1.18-1.34 (m, 8H), 0.84 (t, 6H, J=7.2 Hz); (Note: contain about 5% of 3-substituted isomer).

4-(2-Ethylhexyl)-2-thiophenecarbonitrile

A mixture of 4-(2-ethylhexyl)-2-thiophenecarboxaldehyde (17.3 g, 77.1 mmol) and hydroxylamine hydrochloride salt (8.04 g, 116 mmol) in pyridine/ethanol (40 mL, 1/1, v/v) was refluxed at 85° C. for overnight. After cooling down to room temperature, the solution was rotary evaporated to remove most of the solvent. In a separatory funnel, the residue was taken up with chloroform (100 mL) and washed with distilled water (2×75 mL). After drying over anhydrous magnesium sulfate, the solvent was removed by rotary evaporation to give a yellowish liquid, which was dissolved in acetic anhydride (60 mL). To the resulting solution was added potassium acetate (0.4 g). The solution was then heated up to 140° C. and refluxed for 4 h. After cooling, the yellow solution was dropped into 100 mL of cold water and was extracted with hexane (2×100 mL). The combined organic layers were washed with distilled water twice and then dried over magnesium sulfate. The solvent was removed by rotary evaporation and the residue was subject to a silica-gel column chromatography (EtOAc/Hex=1/10, v/v, Rf=0.5) to yield a colorless liquid product (15.6 g, 91% yield). $^1$H NMR (400 MHz, CDCl$_3$) δ (ppm): 7.40 (d, 1H, J=1.2 Hz), 7.15 (d, 1H, J=1.2 Hz), 2.54 (d, 2H, J=6.8 Hz), 1.52 (m, 1H), 1.20-1.29 (m, 8H), 0.86 (m, 6H). (3-substitution isomer can be removed in chromatography.)

3,6-Bis[4-(2-ethylhexyl)thien-2-yl]-s-tetrazine

To a solution of 4-(2-ethylhexyl)-2-thiophenecarbonitrile (14.1 g, 63.8 mmol) in ethanol (20 mL) was added sulfur powder (1.02 g, 31.9 mmol). Then hydrazine monohydrate (4.84 g, 95.7 mmol) was added into the mixture dropwise. The resulting solution was stirred at room temperature for 30 min and then heated up to 90° C. and stirred for 4 h. After cooling, the solution was rotary evaporated to give a red viscous residue that was dissolved in chloroform (50 mL). To the solution was added isopentylnitrite (12.0 g, 102 mmol). The solution was stirred at room temperature for 24 h. The solvent was removed by rotary evaporation and the viscous residue was subjected to silica-gel column chromatography (EtOAc/Hex=1/15, v/v, Rf=0.4) to yield the deep red liquid product (5.33 g, 36% yield). $^1$H NMR (400 MHz, CDCl$_3$) δ (ppm): 8.05 (s, 2H), 2.62 (4H, d, J=7.2 Hz), 1.61 (m, 2H), 1.28-1.37 (m, 16H), 0.90 (m, 12H); $^{13}$C NMR (100 MHz, CDCl$_3$): δ 161.6, 144.4, 135.5, 132.6, 128.6, 40.6, 34.6, 32.7, 29.1, 25.8, 23.2, 14.3, 11.1.

3,6-Bis[5-bromo-4-(2-ethylhexyl)thien-2-yl]-s-tetrazine

To a solution of 3,6-bis[4-(2-ethylhexyl)thien-2-yl]-s-tetrazine (0.6 g, 1.45 mmol) in a mixture of CHCl$_3$ (15 mL) and glacial acetic acid was added N-bromosuccinimide (0.57 g, 3.18 mmol) at room temperature. The solution heated and stirred at 50° C. for 4 h and 80° C. for 5 h. The solution was subjected to vacuum distillation at about 50° C. to remove solvent completely. The resulting red solid residue was washed with MeOH twice. The product was purified by chromatography through a silica-gel column (CHCl$_3$/hex=2/8, v/v, Rf=0.4) to yield the product (red crystal). (1.17 g, 46% yield). $^1$H NMR (400 MHz, CDCl$_3$): δ 7.89 (s, 2H), 2.56 (d, 4H, J=7.2 Hz), 1.65 (m, 2H), 1.25-1.35 (m, 16 H), 0.88 (m, 12 H); $^{13}$C NMR (100 MHz, CDCl$_3$) δ (ppm): 160.9, 144.1, 135.0, 132.2, 118.8, 40.1, 34.0, 32.7, 29.0, 25.9, 23.2, 14.3, 11.0.

Example 2

Synthesis of PTSiTTz-2,6;2,6 copolymer 4,4'-Bis(2-ethylhexyl)-5,5'bis(trimethylstannyl)-dithieno[3,2-b:2',3'-d]silole 4,4'-bis(ethylhexyl)-dithieno[3,2-b:2',3'-d]silole (1.17 g, 2.79 mmol) was added into a 50 mL flask and purged with Ar under vacuum. 20 ml of dry THF was added into a flask. The solution was cooled down to −78° C. using a dry ice-acetone bath. Then 1.6 M n-butyllithium/hexane solution (3.84 mL, 6.14 mmol) was added dropwise. The temperature was then raised to about room temperature and the solution was stirred for 60 minutes. The solution was cooled to −78° C. again, and 1M trimethyltin chloride/THF (6.98 mL, 6.98 mmol) was added. Then the cooling bath was removed. After being stirred at ambient temperature overnight, 20 mL hexane and 20 mL of H$_2$O was added with stirring, the water layer was separated, the organic layer was washed with 15 mL of H$_2$O again, and the combined water layers were extracted with 20 mL of hexane. The combined organic layers were washed with water again and then dried with MgSO$_4$. After removal of volatiles, 4,4'-bis(ethylhexyl)-5,5'-bis(trimethyltin)-dithieno[3,2-b:2',3'-d]silole was obtained as sticky pale green oil and used without any further purification. $^1$H NMR (400 MHz, CDCl$_3$) δ (ppm): 7.24 (s, 2H), 1.41 (m, 2H), 1.21-1.32 (m, 4H), 1.08-1.21 (m, 12H), 0.92-1.08 (m, 4H), 0.81 (t, 6H, J=7.4 Hz), 0.77 (t, 6H, J=7.4 Hz), 0.38 (s, 18H)

PTSiTTz-2,6;2,6

To a 25 mL flask was added 4,4'-bis(2-ethylhexyl)-5,5' bis(trimethylstannyl)-dithieno[3,2-b:2',3'-d]silole (0.3126 g, 0.420 mmol), 3,6-bis[5-bromo-4-(2-ethylhexyl)thien-2-yl]-s-tetrazine (0.2514 g, 0.400 mmol) N,N-dimethylformamide (DMF, 0.5 mL) and toluene (8 mL). The system was purged with Ar under vacuum. (PPh$_3$)$_4$Pd(0) (0.06 g, 0.006 mmol) was added in a glove box. The solution was stirred and reflux for 24 hr under the protection of Ar. After the solution was cooled down to room temperature, the solution was dropped into acetone to precipitate the copolymer. The copolymer was Soxhlet extracted with n-hexane and then acetone, and then collected with hot toluene to obtain 0.32 g copolymer, (yield 91%). GPC: $M_n$=22,100 Da, $M_w$=59,700 Da, PDI=2.70. $^1$H NMR (CDCl$_3$) δ (ppm): 8.07 (s, 2H); 7.28 (s, 2H); 2.83 (m, 4H); 1.77 (m, 2H); 1.47 (m, 2H); 1.15-1.44 (m, 32H), 1.03 (m, 4H), 0.89 (m, 12H); 0.82 (m, 12H).

Example 3

Synthesis of 3,6-bis(5-bromo-4-hexylthien-2-yl)-s-tetrazine monomer

4-Hexylthiophene-2-carbonitrile

A mixture solution of 4-hexylthiophene-2-carbaldehyde (11.8 g, 60.0 mmol) and hydroxylamine hydrochloride salt (6.3 g, 90 mmol) in pyridine/ethanol (60 mL, 1/1 v/v) was stirred at 80° C. overnight. Then the solvent was removed and the residue was dissolved in chloroform (100 mL). The solution was washed with distilled water (2×50 mL) and dried over anhydrous magnesium sulphate. The solvent was removed and the viscous liquid residue was refluxed in acetic anhydride (30 mL) containing potassium acetate (0.2 g) for 3 h. Then the mixture was poured into distilled water (100 mL) and extracted with hexanes (3×50 mL). The combined organic phase was washed three times with water (50 mL), dried over anhydrous magnesium sulfate before the solvent was removed by rotary evaporation. The yellow liquid residue was purified by silica-gel column chromatography (EtOAc/hexane=7/93, v/v, Rf=0.4) to yield a clear light yellow liquid product. (9.8 g, 84.5% yield). $^1$H NMR (400 MHz, CDCl$_3$) δ (ppm): 7.43 (d, 1H, J=1.4 Hz); 7.17 (d, 1H, J=1.4 Hz); 2.60 (t, 2H, J=8.0 Hz); 1.59 (m, 2H); 1.22-1.36 (m, 6H); 0.87 (m, 3H). $^{13}$C NMR (100 MHz, CDCl$_3$): δ 144.04, 138.22, 127.41, 114.48, 109.28, 31.45, 30.18, 29.86, 28.67, 22.46, 13.96. HRMS EI calcd for C$_{11}$H$_{15}$S 193.0925, found 193.0915.

3,6-Bis(4-hexylthien-2-yl)-s-tetrazine

Fresh hydrazine monohydrate (1.8 g, 35.7 mmol) was added at room temperature to a mixture of 4-hexylthiophene-2-carbonitrile (4.6 g, 23.8 mmol) and sulfur (0.53 g, 16.7 mmol) in anhydrous ethanol (15 mL). The mixture was stirred at room temperature for 30 min. The solution turned yellow and a large amount of gas evolved. The solution was then heated to reflux and stirred for 4 h. Then, the solvent was cooled to room temperature resulting in crystal formation from the solution. The crystals were collected by filtration and rinsed with cold ethanol and then dried under vacuum. To a chloroform solution (50 mL) of the obtained solid, isoamyl nitrite (5.58 g, 47.6 mmol) was added and the solution was stirred at room temperature overnight. The solvent was removed and the resulting red solid was washed with methanol twice before being purified by silica-gel column chromatography (CHCl$_3$/Hexane=4/6, v/v, Rf=0.5) to yield red needle-like crystal (2.0 g, yield: 40.5%). $^1$H NMR (400 MHz, CDCl$_3$): δ 8.07 (d, 2H, J=1.6 Hz); 7.26 (d, 2H); 2.68 (t, 4H, J=7.6 Hz); 1.63-1.71 (m, 4H); 1.29-1.40 (m, 12H); 0.89 (m, 6H). $^{13}$C NMR (100 MHz, CDCl$_3$) δ (ppm): 161.35, 145.46, 135.48, 131.88, 127.57, 31.62, 30.37, 30.34, 28.87, 22.58, 14.08. HRMS EI calcd for C$_{22}$H$_{30}$N$_4$S$_2$ 414.1912, found 414.1895.

3,6-Bis(5-bromo-4-hexylthien-2-yl)-s-tetrazine

To a suspension solution of 3,6-bis(4-hexylthien-2-yl)-s-tetrazine (0.9 g, 1.8 mmol) in chloroform (20 mL) and acetic acid (20 mL) was added N-bromosuccinimide (0.32 g, 1.8 mmol) at room temperature. The mixture was stirred at room temperature in the dark for 1 h before being heated to 80° C. for 5 h. Then, the solution was poured into distilled water (100 mL) and extracted with chloroform (3×30 mL). The organic phase was washed with water and dried over anhydrous magnesium sulfate. The solvent was removed and the residue was purified by silica-gel chromatography (CHCl$_3$/hexane=1/2, v/v, Rf=0.5) to yield the product (0.9 g, yield 87%). $^1$H NMR (400 MHz, CDCl$_3$): δ 7.93 (s, 2H); 2.63 (t, 4H, J=7.6 Hz); 1.65 (m, 4H); 1.28-1.40 (m, 12H); 0.89 (m, 6H). $^{13}$C NMR (100 MHz, CDCl$_3$) δ (ppm): 160.67, 144.59, 134.95, 131.47, 117.94, 31.56, 29.57, 29.45, 28.82, 22.56, 14.06. HRMS EI calcd for C$_{22}$H$_{28}$N$_4$Br$_2$S$_2$ 570.0122, found 570.0127.

Example 4

Synthesis of PCPDTTTZ-6;6 copolymer 4,4'-Dihexyl-5,5'-bis(trimethylstannyl)-cyclopentadithiophene 4,4'-dihexyl-cyclopentadithiophene (1.48 g, 4.20 mmol) was added into a 50 mL flask and purged with Ar under vacuum. 30 ml of dry THF was added into a flask. The solution was cooled to −78° C. using a dry ice-acetone bath. Then 1.6 M n-butyllithium in hexane (5.9 mL, 9.39 mmol) was added dropwise. The temperature was then raised to 0° C. and the solution stirred for 60 minutes. The solution was cooled to −78° C. again, and 1 M trimethyltin chloride in THF (10.7 mL, 10.7 mmol) was added. The cooling bath was removed. After being stirred at ambient temperature for overnight, 20 mL hexane and 15 mL of H$_2$O was added with stirring, the water layer was separated, the organic layer was washed with 15 mL of H$_2$O again, the combined water layers were extracted with 20 mL of hexane, and the combined organic layers were washed with water again and then dried with MgSO$_4$. After removal of volatiles, 4,4'-dihexyl-5,5'bis(trimethylstannyl)-cyclopentadithiophene was obtained as a sticky light green oil and used without any further purification. $^1$H NMR (400 MHz, CDCl$_3$) δ (ppm): 7.18 (S, 2H), 1.88 (m, 4H), 1.10-1.20 (m, 12H), 0.98 (m, 4H) 0.80 (t, J=7.6 Hz, 6H), 0.38 (s, 18H).

PCPDTTTZ-6;6

4,4-dihexyl-2,6-bis(trimethylstannanyl)-4H-cyclopenta[2,1-b:3,4-b']dithiophene (0.2756 g, 0.410 mmol) and 3,6-bis(5-bromo-4-hexylthien-2-yl)-s-tetrazine from Example 3 (0.2290 g, 0.400 mmol) were dissolved in a mixture of 8 mL toluene and 0.8 mL DMF. The mixture were purged with argon under vacuum for 3 times before 6 mg of Pd(PPh$_3$)$_4$ was added in a glove box. The solution was stirred and refluxed for 24 hours under argon and then cooled to room temperature and precipitated in acetone. The resulting copolymer was further purified by Soxhlet extraction with hexanes, acetone and toluene. The copolymer recovered by dichlorobenzene extraction was precipitated in acetone and dried under vacuum for 16 h, to get PCPDTTTZ-6;6 as a dark solid (110 mg, yield: 36%). GPC: M$_n$=20,000 Da, M$_w$=28,200 Da, PDI=1.41. $^1$H NMR (1,2-dichlorobenzene-d$_4$, 100° C.) δ (ppm): 8.11 (s, 2H); 7.37 (s, 2H); 2.91 (t, 4H); 2.05 (br, 4H); 1.78 (m, 4H); 1.46(m, 4H); 1.10-1.40 (m, 24H), 0.89 (t, 6H); 0.82 (t, 6H).

Example 5

Synthesis of 3,6-bis(5-bromo-3-hexylthien-2-yl)-s-tetrazine monomer

3-Hexylthiophene-2-carboxaldehyde

To the solution of 2-bromo-3-hexylthiophene (13.5 g, 54.6 mmol) in anhydrous tetrahydrofuran (200 mL) in a dry ice/acetone bath at −78° C. was added n-butyl lithium (2.5 M in hexane, 24.0 mL, 60.1 mmol) dropwise under the protection of argon. The reaction solution was warmed to −40° C. and stirred for 60 min. The solution was cooled down to −78° C. again, and 1-formylpiperidine (7.41 g, 65.5 mmol) was added in one shot. Then, the solution was allowed to warm slowly up to room temperature and stirred overnight. The solution was then poured into ice water. The organic layer was separated and the aqueous layer was extracted twice with hexane (100 mL). The organic extracts were combined and washed three times with distilled water (50 mL), dried over anhydrous magnesium sulfate, and rotary evaporated to remove the solvent. The liquid residue was subjected to silica-gel column chromatography (EtOAc/hexane=1/10, Rf=0.4) to yield a clear liquid product (9.8 g, 92% yield). $^1$H NMR (400 MHz, acetone-d$_6$) δ (ppm): 10.11 (s, 1H); 7.89 (d, 1H, J=5.2 Hz); 7.17 (d, 1H, J=5.2 Hz); 3.04 (t, 2H, J=7.8 Hz); 1.69 (m, 2H); 1.28-1.42 (m, 6 H); 0.87 (m, 3H).

2-Cyano-3-hexylthiophene

To a solution of 3-hexylthiophene-2-carboxaldehyde (7.8 g, 40 mmol) in pyridine/ethanol (60 mL, 1/1, v/v) was added hydroxylamine hydrochloride salt (4.2 g, 60 mmol). The solution was stirred with refluxing at 80° C. overnight. After cooling, the solution was rotary evaporated to remove the solvent. The residue was taken up with chloroform (100 mL) and the resulting solution was washed twice with distilled water (50 mL), dried over anhydrous magnesium sulfate, and rotary evaporated to remove the solvent. The viscous liquid residue was then dissolved in acetic anhydride (30 mL) containing 0.2 g of potassium acetate, and the resulting mixture was refluxed at 140° C. for 3 h. After cooling down to room temperature, the solution was poured into 100 mL H$_2$O and extracted three times with hexanes (50 mL). The organic extracts were combined and washed until neutral, dried over anhydrous magnesium sulfate, and rotary evaporated to remove the solvent. The yellow liquid residue was subjected to silica-gel column chromatography (EtOAc/Hex=8/92, v/v, Rf=0.4) to yield a light yellow liquid product (5.0 g, 65% yield). $^1$H NMR (400 MHz, acetone-d6) δ (ppm): 7.85 (d, 1H, J=5.2 Hz); 7.19 (d, 1H, J=5.2 Hz); 2.80 (t, 2H, J=7.8 Hz); 1.68 (m, 2H); 1.28-1.38 (m, 6 H); 0.88 (m, 3H).

3,6-Bis(3-hexylthien-2-yl)-s-tetrazine 2-cyano-3-hexylthiophene (3.95 g, 20.4 mmol), sulfur (0.39 g, 12.3 mmol) and ethanol (15 mL) were added into a 50 mL round-bottom flask, which was equipped with a magnetic stir bar and was then sealed with a rubber septum. The reaction system was connected to a thick-wall rubber balloon for regulating the pressure inside the flask during the reaction. Anhydrous hydrazine (95%, 2.0 g, 40.8 mmol) was added into the solution using a syringe at room temperature. The temperature was then raised to 50° C. The solution turned to brown with gas evolved. The sulfur in the solution was completely dissolved within 5 min, and then the temperature was increased to 68° C. The solution was stirred at 68° C. with the pressure regulated by the thick-wall rubber balloon. $2^{nd}$ and $3^{rd}$ portion of anhydrous hydrazine (95%, 1.0 g, 20.4 mmol each) were added in 6 hrs interval. The reaction was stopped in 20 hrs by cooling to room temperature, where the solution turned to slurry. It was mixed with 15 mL of MeOH and then filtered to collect the solid, which was rinsed with MeOH and dried in air for 30 min to give a pale white powder. $^1$H NMR (400 MHz, C$_6$D$_6$): δ 6.84 (s, 2H), 6.64 (d, J=5.0 Hz, 2H); 6.55 (d, J=5.0 Hz, 2H); 2.71 (t, J=7.8 Hz, 4H); 1.51 (m, 4H); 1.14-1.26 (m, 12H) 0.85 (t, J=7.2 Hz, 6H).

The resulting powder was then dissolved in 20 mL of CHCl$_3$ and isoamyl nitrite (5.5 g, 47 mmol) was added, and was stirred at 40° C. for 8 hrs. The solvent was removed by a rotary evaporation and the resulting red solid was washed with methanol twice, and then subjected to re-crystallization in 2-propanol to yield red needle-like crystal (2.7 g, 65% yield). $^1$H NMR (400 MHz, CDCl$_3$): δ 7.54 (d, J=5.0 Hz, 2H); 7.09 (d, J=5.0 Hz, 2H); 3.23 (t, J=7.6 Hz, 4H); 1.69 (m, 4H); 1.41 (m, 4H); 1.26-1.34 (m, 8H) 0.87 (t, J=7.2 Hz, 6H). $^{13}$C NMR (100 MHz, CDCl$_3$): δ 161.8, 149.3, 132.0, 130.7, 129.3, 31.7, 30.5, 30.3, 29.1, 22.6, 14.1.

3,6-Bis[2-bromo-3-hexylthien-2-yl]-s-tetrazine

To a solution of 3,6-bis(2-hexylthien-2-yl)-s-tetrazine (0.22 g, 0.53 mmol) in CH$_2$Cl$_2$ (5 mL) was added N-bromosuccinimide (0.75 g, 4.24 mmol) and silica gel (0.05 g) at 20° C. The mixture was stirred at room temperature overnight. The solution was poured into distilled water (20 mL) and extracted with CH$_2$Cl$_2$ (3×30 mL). The organic extracts were combined and washed with distilled water, dried over anhydrous magnesium sulfate and rotary evaporated to remove the solvent. The resulting liquid residue was subjected to silica-gel chromatography (20% CHCl$_3$/hexanes, v/v, Rf=0.5) to yield the red solid product (0.24 g, 80% yield). $^1$H NMR (400 MHz, CDCl$_3$), δ (ppm): 7.03 (s, 2H); 3.14 (t, 4H, J=7.8 Hz); 1.63 (m, 4H); 1.24-1.31 (m, 12H); 0.85 (m, 6H). $^{13}$C NMR (400 MHz, CDCl$_3$) δ (ppm): 161.0, 150.0, 134.8, 130.7, 119.5, 31.6, 30.5, 30.1, 29.0, 22.5, 14.1.

Example 6

Synthesis of PCPDTTTz-6;In6 copolymer 4,4-dihexyl-2,6-bis(trimethylstannanyl)-4H-cyclopenta[2,1-b:3,4-b']dithiophene from Example 4 (0.2371 g, 0.353 mmol) and 3,6-bis(5-bromo-4-hexylthien-2-yl)-s-tetrazine (0.2019 g, 0.353 mmol) were dissolved in a mixture of 8 mL toluene and 0.8 mL DMF. The mixture were purged with argon under vacuum 3 times before 6 mg of Pd(PPh$_3$)$_4$ was added in a glove box. The solution was stirred and refluxed for 24 hours under argon and then cooled to room temperature and precipitated in acetone. The resulting copolymer was further purified by Soxhlet extraction with hexanes and then acetone. The copolymer recovered by dichlorobenzene extraction was precipitated in acetone and dried under vacuum for 16 h, to get PCPDTTTz-6;In6 as a dark solid (0.20 mg, yield: 62%). GPC: $M_n$=15,800 Da, $M_w$=28,200 Da, PDI=1.78.

Example 7

Synthesis of PFTTz-8;6 copolymer (see Scheme 5)

3,6-bis(5-bromo-4-hexylthien-2-yl)-s-tetrazine from Example 3 (0.2962 g, 0.50 mmol) and 9,9-dioctylfluorene-2,7-bis(ethyleneboronate) (0.2652 g, 0.50 mmol), Aliquat™ 336 (1 drop), toluene (8 mL) and 2M Na$_2$CO$_3$ aqueous solution (4 mL) were added into a 25 mL flask. The system was degassed and by purging with argon three times. Then, Pd(PPh$_3$)$_4$ (about 6 mg) was added in a glove box. The mixture was heated at reflux with stirring for 24 h. The reaction mixture was cooled down. The organic layer was poured slowly into 100 mL methanol/acetone (1/1 by volume) with agitation. The obtained red fibre-like copolymer was collected by filtration, washed with acetone, and dried under vacuum (0.34 g, yield: 85%). GPC: $M_n$=23,500 Da, $M_w$=33,000 Da, PDI=1.40. $^1$H NMR (CDCl$_3$): δ 8.18 (s, 2H); 7.75-7.87 (m, 2H); 7.41-7.60 (m, 4H); 2.79 (m, 4H); 2.04 (m, 4H) 1.73 (m, 4H); 1.10-1.43 (m, 32H); 0.87 (m, 6H); 0.80 (m, 10H).

Example 8

Synthesis of PBDTTTz-4,8;6 copolymer (see Scheme 5)

3,6-bis(5-bromo-4-hexylthien-2-yl)-s-tetrazine (0.1723 g, 0.30 mmol), 2,6-bis(trimethylstanenne)-4,8-bis(3-butyloctyl)-benzo[1,2-b:4,5-b']dithiophene (0.2558 g, 0.30 mmol) and toluene (10 mL) were added into a 25 mL flask. The system was degassed by purging with argon three times. Then, Pd(PPh$_3$)$_4$ (about 6 mg) was added in a glove box. The mixture was heated at reflux with stirring for 24 h. The reaction mixture was cooled and dropped into 100 mL of methanol/acetone (1/1 by volume) with agitation. The obtained deep red fibre-like powder was collected by filtration, washed with acetone, and dried under vacuum (0.26 g, yield: 92%). GPC: M$_n$=16,800 Da, M$_w$=33,800 Da, PDI=2.01.

Example 9

Copolymer Characterization—Molecular Weight and Cyclic Voltammetry

Table 1 provides molecular weight and energy level characterization for selected copolymers of the present invention. Molecular weights were determined from gel permeation chromatography (GPC) analysis. HOMO and LUMO energy levels and energy gap (E$_g$) values were determined from cyclic voltammetry analysis.

TABLE 1

| # | Copolymer | Mn (Da) | Mw (Da) | LUMO (eV) | HOMO (eV) | E$_g$ (eV) |
|---|---|---|---|---|---|---|
| S1019 | PTSiTTz-2,6;2,6 | 22,100 | 59,700 | −3.47 | −5.10 | 1.63 |
| S1030 | PCPDTTTz-2,6;2,6 | 17,000 | 34,000 | −3.59 | −5.19 | 1.60 |
| S1033 | PCPDTTTz-6;2,6 | 11,900 | 25,500 | −3.57 | −5.06 | 1.49 |
| S1044 | PCPDTTTz-2,6;6 | 29,400 | 44,500 | −3.61 | −5.16 | 1.55 |
| S1045 | PCPDTTTz-2,6;In6 | 48,000 | 87,500 | −3.58 | −5.01 | 1.43 |
| S1047 | PCPDTTTz-6; 6 | 20,000 | 28,100 | −3.58 | −4.95 | 1.37 |
| S9003 | PFTTz-8; 6 | 23,500 | 33,000 | −3.53 | −5.68 | 2.15 |
| S9005 | PBDTTTz-4,8; 6 | 16,800 | 33,800 | −3.60 | −5.39 | 1.79 |

Figure 4:
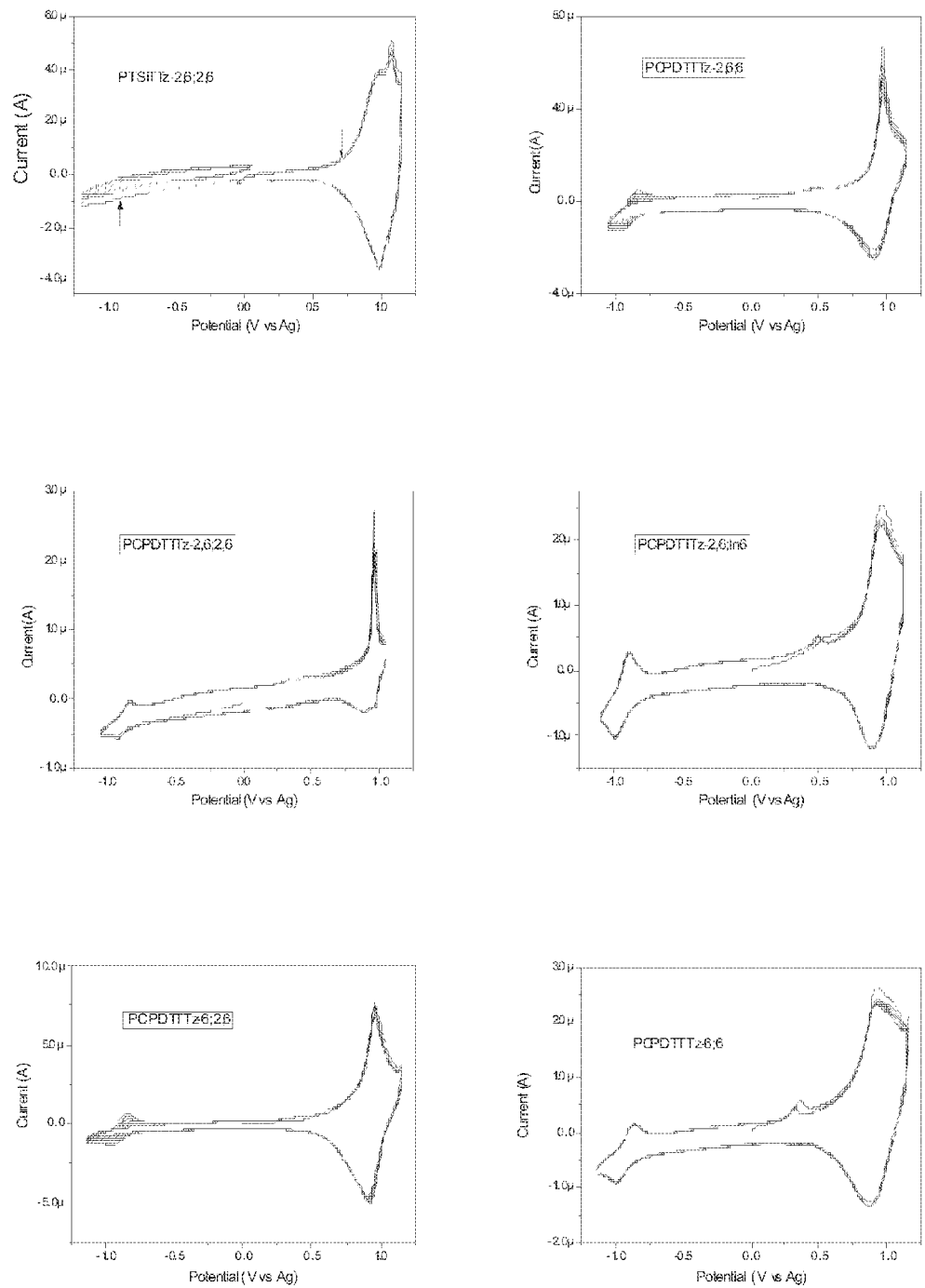
FIG. 4 depicts cyclic voltammograms of selected tetrazine-containing copolymers of the present invention.

HOMO and LUMO energy levels of copolymers were measured by cyclic voltammetry (CV), with the CV results for some selected copolymers shown in FIG. 4. It can be seen that all the tetrazine-containing copolymers have a reversible reduction wave and a reversible oxidation wave. Generally, the intensity of the oxidation wave of the copolymer is much larger than the reduction wave, indicating that the materials are good hole transporters making them ideal for use as electron donors. Interestingly, as the size of the side group on the TTz unit is reduced from C8 to C6, the intensity of the reduction wave increases significantly, indicating a dramatic increase in electron accepting capability.

Energy gaps calculated from the HOMO and LUMO values (Table 1) are slightly small than the values obtained from optical measurements (Example 8). This is probably due to a crystalline structure formed in the films, which results in a slightly broad oxidation wave in the CV curve leading to a calculated HOMO value higher than the one as measured by UV spectroscopy.

Example 10

Copolymer Characterization—UV-Visible Spectroscopy

Figure 5:
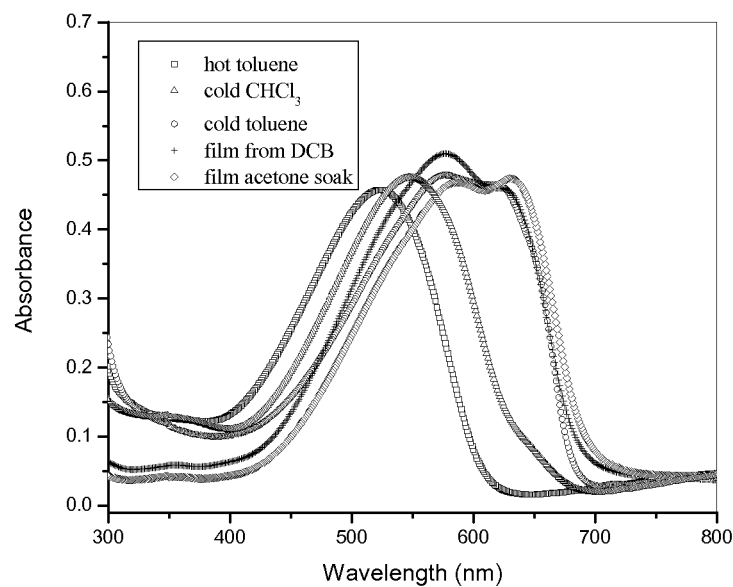
FIG. 5 depicts UV-vis spectra of PTSiTTz-2,6;2,6 in solutions and in film.

All of the copolymers show a strong solvatochromic effect in their UV-vis spectra. FIG. 5 compares UV-vis spectra of PTSiTTz-2,6;2,6 in different solutions and in film. The film spectra are red shifted by more than 100 nm (523 to 631 nm) compared to the solution spectra. The UV-vis spectrum of the copolymer in hot toluene peaked at 521 nm. At room temperature, the peak became broad having two maxima centered at 577 nm and 620 nm, and having a red shift of about 100 nm, indicating that the copolymer chains possess a more conjugated structure in the toluene solution at room temperature. This phenomenon is attributed to the formation of small size close packing of the copolymer chains in solution. A copolymer film coated from DCB solution at about 60° C. shows a similar UV-vis spectrum to that in the toluene solution at room temperature, having a red shift of about 10 nm more indicating slightly higher conjugation in the copolymer chain. Thermal and solvent vapor annealing or solvent soaking of the film enhances this chain packing and promotes absorption at longer wavelengths as shown in FIG. 5.

Figure 6:
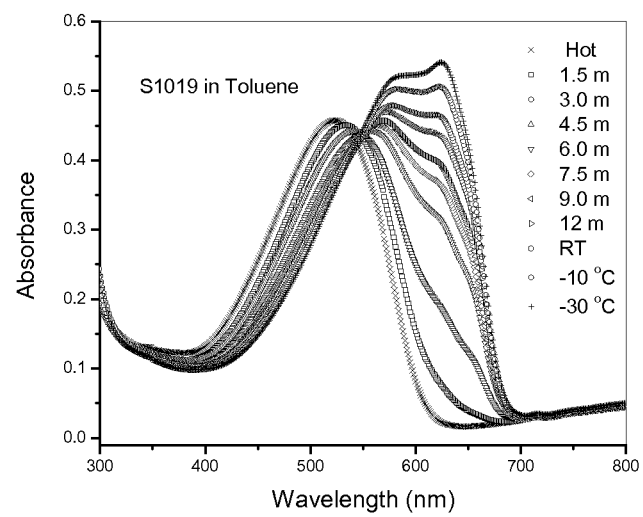
FIG. 6 depicts UV-vis spectra of PTSiTTz-2,6;2,6 in toluene at different temperatures.

This solvatochromic effect was further studied in toluene at different temperatures. The toluene solution in a UV cuvette was heated to a temperature close to boiling. Then, UV spectra were recorded in 1.5 min intervals as the solution cooled. The results in FIG. 6 clearly show a strong close packing tendency of the copolymer chain in toluene.

One of the advantages of the copolymers of the present invention is their extremely high light absorption both in solution and in film. The molar absorptivity ($\epsilon_{max}$, M$^{-1}$cm$^{-1}$) of PTSiTTz-2,6;2,6 is 4.67×10$^4$ and 4.61×10$^4$ in toluene and in CHCl$_3$, corresponding to a very high weight absorptivity ($\epsilon_w$, mL·g$^{-1}$cm$^{-1}$) of 5.27×10$^4$ and 5.21×10$^4$, respectively, due to the small size of the repeat unit of the copolymer.

Figure 7:
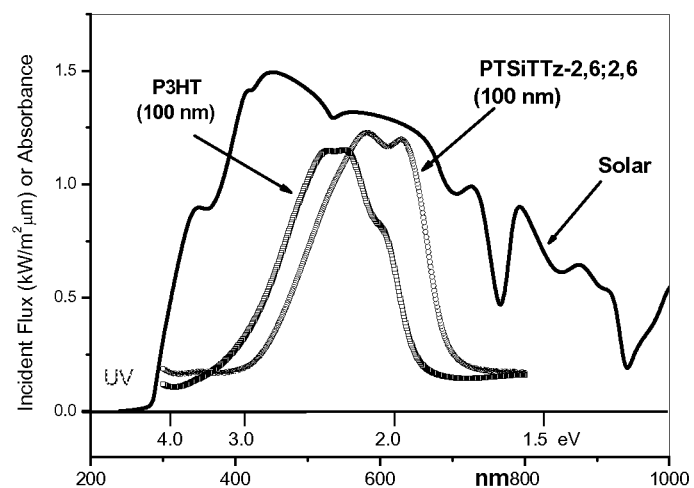
FIG. 7 depicts UV-vis spectra of the P3HT and PTSiTTz-2,6;2,6 films compared with the solar spectrum.

The film UV-vis spectrum of PTSiTTz-2,6;2,6 was compared to that of P3HT on samples normalized to a thickness of 100 nm. FIG. 7 shows that the tetrazine copolymer has absorption maxima red shifted by about 70 nm compared to the maxima of P3HT (i.e. about 630 nm for PTSiTTz-2,6;2,6 compared to 550 nm for P3HT). The solar spectrum is overlaid in FIG. 7.

Figure 8:
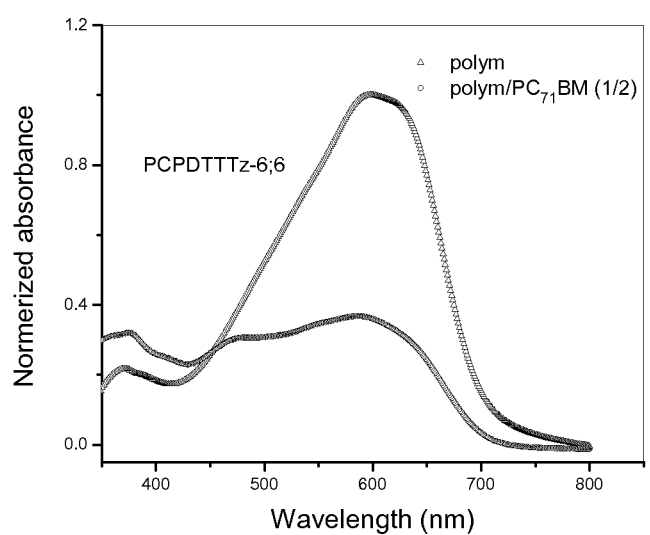
FIG. 8 depicts UV-vis spectra of PCPDTTTZ-6;6 pure polymer film and a blended film with $PC_{71}BM$ (1/2, v/v)

With reference to FIG. 8, the UV-vis absorption spectra of a pure copolymer film of PCPDTTTZ-6;6 and a film of PCPDTTTZ-6;6 blended with PC$_{71}$BM (1/2, v/v) demonstrates that the film of the blend has strong absorption over a wide region of the spectrum. Film thicknesses were normalized to 100 nm. Films comprising a blend of PCPDTTTZ-6;6 and PC$_{71}$BM strongly absorb over such a wide region since PCBM has a fairly strong absorption at shorter wavelengths (PC$_{71}$BM has an absorption maximum at about 450 nm), while PCPDTTTZ-6;6 has a strong absorption at longer wavelengths (PCPDTTTZ-6;6 has absorption maxima at about 600 nm and 630 nm). The solid film of pure PCPDTTTZ-6;6 copolymer exhibits a broad strong absorption with two maxima at about 600 nm and 630 nm due to interchain close packing (an o-dichlorobenzene solution of PCPDTTTZ-6;6 has an absorption maximum at about 587 nm). The onset absorption for the film of pure PCPDTTTZ-6;6 copolymer is at about 760 nm, corresponding to an optical band gap of about 1.63 eV (onset of absorption for the o-dichlorobenzene solution of PCPDTTTZ-6;6 is at about 723 nm). After blending with PC$_{71}$BM in a volume ratio of 1/2, the formed film showed a broad absorption in a range from about 450 nm to about 650 nm.

Example 11

Copolymer Characterization—Thermal Analysis

Figure 9:
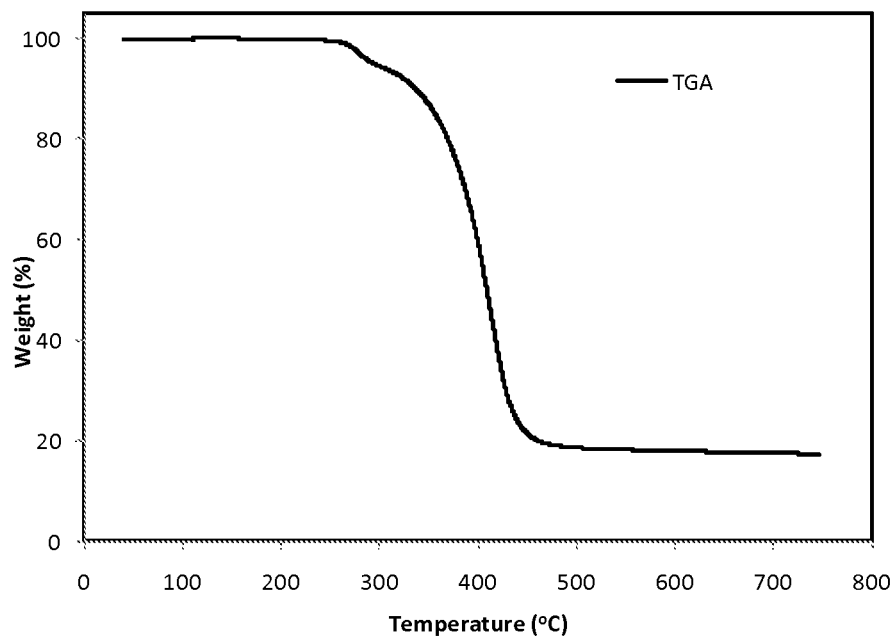
FIG. 9 depicts a TGA curve of PCPDTTz-6;6 with a heating rate of 10° C./min.
Figure 10:
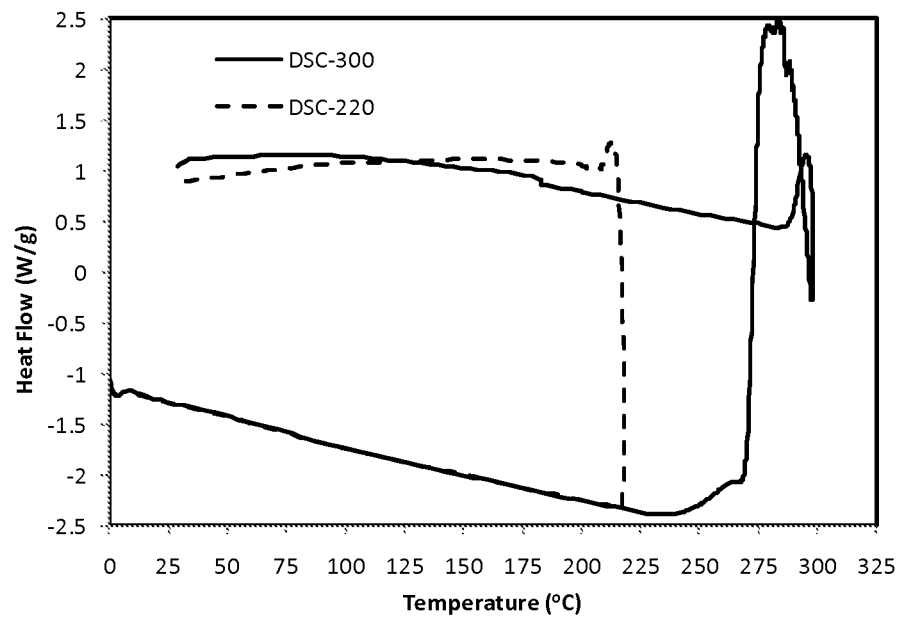
FIG. 10 depicts DSC curves of PCPDTTz-6;6 with a scanning rate of 10° C./min, where the dashed line is a 0° C. to 220° C. scan and the solid line is a 0° C. to 300° C. scan.

Thermal gravimetric analysis (TGA) curve for PCP-DTTTz-6;6 is shown in FIG. 9 and demonstrates that this copolymer has good thermal stability up to about 250° C. Differential scanning calorimetry (DSC) analysis as depicted in FIG. 10 also demonstrates good thermal stability up to about 240° C. under nitrogen atmosphere and reveals no obvious glass transition. The good thermal stability of the copolymers of the present invention is advantageous for their use in electronic device applications, especially solar cells. However, a big exothermic peak was observed starting at about 250° C. in the DSC curve corresponding to decomposition of the tetrazine unit in the polymer main chain with evolution of nitrogen gas. This observation provides direct evidence for the thought that some tetrazine compounds are quite stable although others are employed as energetic materials (Clavier 2010).

Example 12

Solar Cells Fabricated from PCPDTTTz-6;6

Polymer solar cells were fabricated based on PCPDTTTz-6;6 and (6,6)-phenyl-$C_{71}$-butyric acid methyl ester ($PC_{71}BM$) with a general device structure of ITO/PEDOT-PSS/PCPDTTTz-6;6:$PC_{71}MB$/LiF/Al. The active layer of the device is PCPDTTTz-6;6/$PC_{71}BM$ (1/2, v/v).

Thus, indium tin oxide (ITO) patterned glass substrates were washed with detergent before sonicating in CMOS grade acetone and isopropanol for 15 min. The organic residue was further removed by treating with UV-ozone for 10 min. Then a thin layer of poly(3,4-ethylenedioxythiophene) poly(styrenesulfonate) (PEDOT:PSS; Clevios P, H. C. Starck, 45 nm) was spin-coated on the ITO layer and dried for 1 h at 120° C. A blend of PCPDTTTz-6;6 and $PC_{71}BM$ (ADS) (1/2 weight ratio) was dissolved in a mixture of o-dichlorobenzene and diiodooctane (2.5% v/v) at 100° C. The solution was filtered and spin-coated on top of the PEDOT:PSS layer. The border of the PEDOT:PSS layer and active layer was mechanically removed before a 0.7 nm LiF layer and a 100 nm Al layer were deposited by thermal evaporation at a pressure of $5 \times 10^{-7}$ mbar in a Boc Edwards Auto 500 System under a mask. The active area is 50 $mm^2$.

Current-voltage (J-V) characteristics were measured with a Keithley 2400 digital source meter under simulated air mass (AM) 1.5 solar irradiation of 100 mW/$cm^2$ (Sciencetech Inc., SF150). The light intensity was calibrated with a power meter (Gentec Solo PE Laser Power & Energy Meter). The EQE (external quantum efficiency) data was acquired with home-made equipment comprising a monochromator (Newport 90015832), a Stanford Research Systems SR570 lock-in amplifier (locked to light chopped at 30 Hz) and a calibrated silicon diode.

Figure 12:
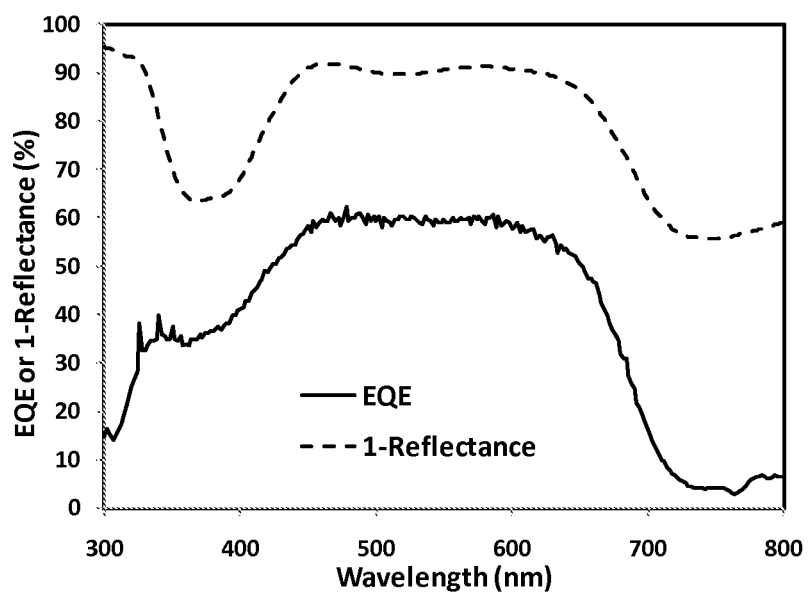

$PC_{71}BM$ was employed because of its enhanced absorption in the visible region. A weight ratio of 1/2 was used for the PCPDTTTz-6;6 and $PC_{71}BM$ to balance electron and hole transport. The active layer was spin coated at 100° C. from o-dichlorobenzene solution because of limited solubility of PCPDTTTz-6;6 at room temperature. Diiodooctane (2.5% v/v) was added as a processing additive to control the BHJ morphology (Lee 2008; Peet 2007). The active layer shows strong absorption in a very wide region from 350 nm to 700 nm (see FIG. 12).

Figure 11:
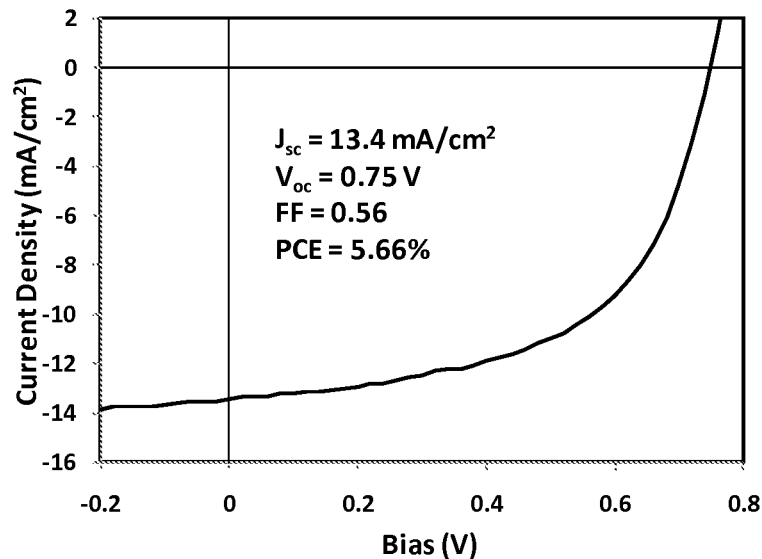
FIG. 11 depicts a current-voltage (J-V) curve for a PCPDTTTz-6;6/$PC_{71}BM$ based solar cell device under illumination of AM 1.5 G, 100 mW/cm²; and, FIG. 12 depicts total absorption (1-reflectance) and EQE spectra for a PCPDTTTz-6;6/$PC_{71}BM$ based solar cell device under illumination of AM 1.5 G, 100 mW/cm².

FIG. 11 shows a typical current density-voltage curve (J-V) with a $V_{OC}$ of 0.75 V, a short-circuit current density ($J_{SC}$) of 13.4 mA/$cm^2$, and a fill factor (FF) of 0.56. The PCE thus reached 5.66%. The $V_{OC}$ of this device is about 0.15 V higher than other CPDT-based polymers (about 0.6 V) (Coppo 2003; Asawapirom 2001; Mühlbacher 2006; Zhu 2007; Lee 2008; Peet 2007) due to the much lower HOMO level of the PCPDTTTz-6;6 copolymer. The external quantum efficiency (EQE) curve (FIG. 12) exhibits a broad response covering 350 nm to 700 nm with about 60% of the response from about 450 nm to about 650 nm, which is among the best values reported for a low band gap polymer based solar cell (Park 2009; Liang 2010; Liang 2009a; Chen 2009; Hou 2009). A 9% difference between the $J_{SC}$ and the integral of the EQE is observed due to spectral mismatch.

References: The contents of the entirety of each of which are incorporated by this reference.

Abdel-Rahman M O, Kira M A, Tolba M N. (1968) A Direct Synthesis of Dihydrotetrazine. *Tetrahedron Letters*. 35, 3871-3872.

Asawapirom U, Scherf U. (2001) Dialkylcyclopentadithiophene Polymers and Copolymers. *Macromol. Rapid Commun.* 22, 746-749.

Audebert P, Sadki S, Miomandre F, Clavier G. (2004a) First example of an electroactive polymer issued from an oligothiophene substituted tetrazine. *Electrochemistry Communications*. 6, 144-147.

Audebert P, Sadki S, Miomandre F, Clavier G, Vernieres M C, Saoud M, Hapiot P. (2004b) *New J. Chem.* 28, 387.

Audebert P. (2006a) *J. Phys. Chem. A.* 110, 12971-12975.

Audebert P. (2006b) *Chem. Commun.* 3612-3614.

Audebert P. (2009a) *J. Electroanal. Chem.* 632, 201-205.

Audebert P. (2009b) *Eur. J. Org. Chem.* 6121-6128.

Chen L-M, Hong Z, Li G, Yang Y. (2009a) Recent Progress in Polymer Solar Cells: Manipulation of Polymer: Fullerene Morphology and the Formation of Efficient Inverted Polymer Solar Cells. *Adv. Mater.* 21, 1434-1449.

Chen H-Y, Hou J, Zhang S, Liang Y, Yang G, Yang Y, Yu L, Wu Y, Li G. (2009b) Polymer solar cells with enhanced open-circuit voltage and efficiency. *Nature photonics*. 3, 649-653.

Cheng Y-J, Yang S-H, Hsu C-S. (2009) Synthesis of Conjugated Polymers for Organic Solar Cell Applications. *Chem. Rev.* 109, 5868-5923.

Clavier G, Audebert P. (2010) s-Tetrazines as Building Blocks for New Functional Molecules and Molecular Materials. *Chem. Rev.* 110, 3299-3314.

Coffin R C, Peet J, Rogers J, Bazan G C. (2009) Streamlined microwave-assisted preparation of narrow-bandgap conjugated polymers for high performance bulk heterojunction solar cells. *Nature Chemistry.* 1, 657.

Coppo P, Cupertino D C, Yeates S G, Turner M L. (2003) Synthetic Routes to Solution-Processable Polycyclopentadithiophenes. *Macromolecules*. 36, 2705-2711.

Dennler G, Scharber M C, Brabec C J. (2009) Polymer-Fullerene Bulk-Heterojunction Solar Cells. *Adv. Mater.* 21, 1323-1338.

Dumas-Verdes C, Miomandre F, Lépicier E, Galangau O, Vu T T, Clavier G, Méallet-Renault R, Audebert P. (2010) BODIPY-Tetrazine Multichromophoric Derivatives. *Eur. J. Org. Chem.*, 113, 2525-2535.

Forrest S R. (2004) *Nature*. 428, 911.

Günes S, Neugebauer H, Sariciftci N S. (2007) Conjugated Polymer-Based Organic Solar Cells. *Chem. Rev.* 107, 1324-1338.

Halls J J M, Walsh C A, Greenham N C, Marseglia E A, Friend R H, Moratti S C, Holmes A B. (1995) *Nature*. 376, 498-500.

Hou J, Chen H-Y, Zhang S, Chen R I, Yang Y, Wu Y, Li G. (2009) Synthesis of a Low Band Gap Polymer and Its Application in Highly Efficient Polymer Solar Cells. *J. Am. Chem. Soc.* 131, 15586-15587.

Hoven C V, Dang X-D, Coffin R C, Peet J, Nguyen T-Q, Bazan G C. (2010) Improved Performance of Polymer Bulk Heterojunction Solar Cells Through the Reduction of Phase Separation via Solvent Additives. *Adv. Mater.* 22, E1-E4, adma. 200903677.

Jung I H, Jung Y K, Lee J, Park J-H, Woo H Y, Lee J-I, Chu H Y, Shim H-K. (2008) *Journal of Polymer Science: Part A: Polymer Chemistry.* 46, 7148-7161.

Kaim W. (2002) The coordination chemistry of 1,2,4,5-tetrazines. *Coordination Chemistry Reviews.* 230 (2002) 127-139.

Lee J K, Ma W L, Brabec C J, Yuen J, Moon J S, Kim J Y, Lee K, Bazan G C, Heeger A J. (2008) Processing Additives for Improved Efficiency from Bulk Heterojunction Solar Cells. *J. Am. Chem. Soc.* 130, 3619-3623.

Li G, Shrotriya V, Yao Y, Huang J, Yang Y. (2007) *J. Mater. Chem.* 17, 3126.

Liang Y, Xu Z, Xia J, Tsai S-T, Wu Y, Li G, Ray C, Yu L. (2010). For the Bright Future—Bulk Heterojunction Polymer Solar Cells with Power Conversion Efficiency of 7.4%. *Adv. Mater.* 22, E135-E138.

Liang Y, Feng D, Wu Y, Tsai S-T, Li G, Ray C, Yu L. (2009a) Highly Efficient Solar Cell Polymers Developed via Fine-Tuning of Structural and Electronic Properties. *J. Am. Chem. Soc.* 131, 7792-7799.

Liang F, Lu J, Ding J, Movileanu R, Tao Y. (Liang 2009b) Design and Synthesis of Alternating Regioregular Oligothiophenes/Benzothiadiazole Copolymers for Organic Solar Cells. *Macromolecules.* 42, 6107-6114.

Ma W, Yang C, Heeger A J. (2005) *Adv. Funct. Mater.* 15, 1617.

Mayer A C, Scully S R, Hardin B E, Rowell M W, McGehee M D. (2007) Polymer-based solar cells. *Material Today.* 10(11), 28-33.

Miyaura N, Suzuki A. (1995) Palladium-Catalyzed Cross-Coupling Reactions of Organoboron Compounds. *Chem. Rev.* 95(7), 2457-2483.

Mühlbacher D, Scharber M, Morana M, Zhu Z, Waller D, Gaudiana R, Brabec C J. (2006) High Photovoltaic Performance of a Low-Bandgap Polymer. *Adv. Mater.* 18, 2884-2889.

Palmas P, et. al. (2007) *Magn. Reson. Chem.* 45, 65-71.

Pasquinet E, et. al. (2007) *Tetrahedron.* 63, 11189-11194.

Park S H, Roy A, Beaupré S, Cho S, Coates N, Moon J S, Moses D, Leclerc M, Lee K, Heeger A J. (2009) Bulk heterojunction solar cells with internal quantum efficiency approaching 100%. *Nature photonics.* 3, 297-303.

Peet J, Kim J Y, Coates N E, Ma W L, Moses D, Heeger A J, Bazan G C. (2007) Efficiency enhancement in low-bandgap polymer solar cells by processing with alkane dithiols. *Nature Materials.* 6, 497.

Pinner, A. (1893) Pinner synthesis of tetrazine. *Chem. Ber.* 26, 2126.

Sagot E, Le Roux A, Soulivet C, Pasquinet E, Poullain D, Girard E, Palmas P. (2007) Synthesis of linear and hyperbranched tetrazine-based polyhetarylene assemblies with high nitrogen content. *Tetrahedron.* 63 (2007) 11189-11194.

Saracoglu N. (2007) Recent advances and applications in 1,2,4,5-tetrazine Chemistry. *Tetrahedron.* 63, 4199-4236.

Sayed A R, Wiggins J S. (2008) 1,3-Dipolar cycloaddition polymerization reactions of novel macromolecules containing sym-tetrazine rings. *Polymer.* 49 (2008) 2253-2259.

Scharber M C, Mühlbacher D, Koppe M, Denk P, Waldauf C, Heeger A J, Brabec C J. (2006) Design Rules for Donors in Bulk-Heterojunction Solar Cells—Towards 10% Energy-Conversion Efficiency. *Adv. Mater.* 18, 789-794.

Soci C, Hwang I-W, Moses D, Zhu Z, Waller D, Gaudiana R, Brabec C J, Heeger A J. (2007) *Adv. Funct. Mater.* 17, 632-636.

Soloducho J, Doskocz J, Cabaj J, Roszak S. (2003) Practical synthesis of bis-substituted tetrazines with two pendant 2-pyrrolyl or 2-thienyl groups, precursors of new conjugated polymers. *Tetrahedron.* 59, 4761-4766.

Stille J K. (1986) *Angew. Chem. Int. Ed.* 25, 508-524.

Tang C W. (1986) *Appl. Phys. Lett.* 48, 183-184.

Thompson B C, Fréchet JMJ. (2008) Polymer-Fullerene Composite Solar Cells. *Angew. Chem. Int. Ed.* 47, 58-77.

Topp K-D, Grote M. (1996) Synthesis and characterization of a 1,2,4,5-tetrazine-modified ion-exchange resin. *Reactive & Functional Polymers.* 3(1), 117-136.

Wang E-C. Lin G-J. (1998) A New One Pot Method for the Conversion of Aldehydes into Nitriles Using Hydroxyamine and Phthalic Anhydride. *Tetrahedron Lett.* 39, 4047-4050.

Wiggins J S, et. al. (2008) *Polymer.* 49, 2253-2259.

Yu G, Heeger A J. (1995) *J. Appl. Phys.* 78, 4510-4515.

Zhu Z, Waller D, Gaudiana R, Morana M, Mühlbacher D, Scharber M, Brabec C. (2007) Panchromatic Conjugated Polymers Containing Alternating Donor/Acceptor Units for Photovoltaic Applications. *Macromolecules.* 40, 1981-1986.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A copolymer of formula (I):

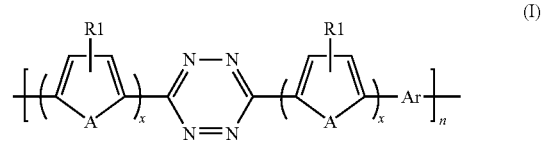

where each A is S, Se or C=C; each x is an integer from 1 to 4; each R1 is independently H, F, CN or a $C_1$-$C_{20}$ linear or branched aliphatic group; Ar is one or more substituted or unsubstituted aromatic units; and, n is an integer 5 or greater.

2. The copolymer according to claim 1, wherein n is an integer in a range of from 5 to 10,000.

3. The copolymer according to claim 1, wherein n is an integer in a range of from 10 to 2,000.

4. The copolymer according to claim 1, wherein Ar has a cyclic structure comprising one or more aryl and/or heteroaryl rings comprising from 2 to 50 carbon atoms, each heteroaryl ring containing 1, 2 or 3 heteroatoms in the ring, the heteroatoms in the heteroaryl rings being one or more of N, O, S or Se.

5. The copolymer according to claim 4, wherein each aryl ring is a $C_6$-aromatic ring.

6. The copolymer according to claim 4, wherein the heteroatoms in the heteroaryl rings are N, S or both N and S.

7. The copolymer according to claim 1, wherein substituents on Ar are one or more of halo, cyano, hydroxy, oxo, amino, amido, carboxy, nitro, thio, $C_1$-$C_{20}$-alkyl, $C_2$-$C_{20}$-alkenyl, $C_2$-$C_{20}$-alkynyl, $C_6$-$C_{20}$-aryl, $C_7$-$C_{24}$-alkaryl, $C_1$-$C_{20}$-alkoxy, $C_2$-$C_{20}$-alkenoxy, $C_2$-$C_{20}$-alkynoxy, $C_6$-$C_{20}$-aryloxy, $C_1$-$C_{20}$-alkylamino, $C_2$-$C_{40}$-dialkylamino, $C_1$-$C_{20}$-alkamido, $C_2$-$C_{20}$-carboxy or $C_1$-$C_{20}$-carbonyl.

8. The copolymer according to claim 1, wherein substituents on Ar are one or more of F, R2 or OR2, where R2 is a $C_1$-$C_{20}$ linear or branched alkyl group.

9. The copolymer according to claim 1, wherein substituents on Ar are R2, wherein each R2 is independently hexyl or 2-ethylhexyl.

10. The copolymer according to claim 1, wherein Ar is

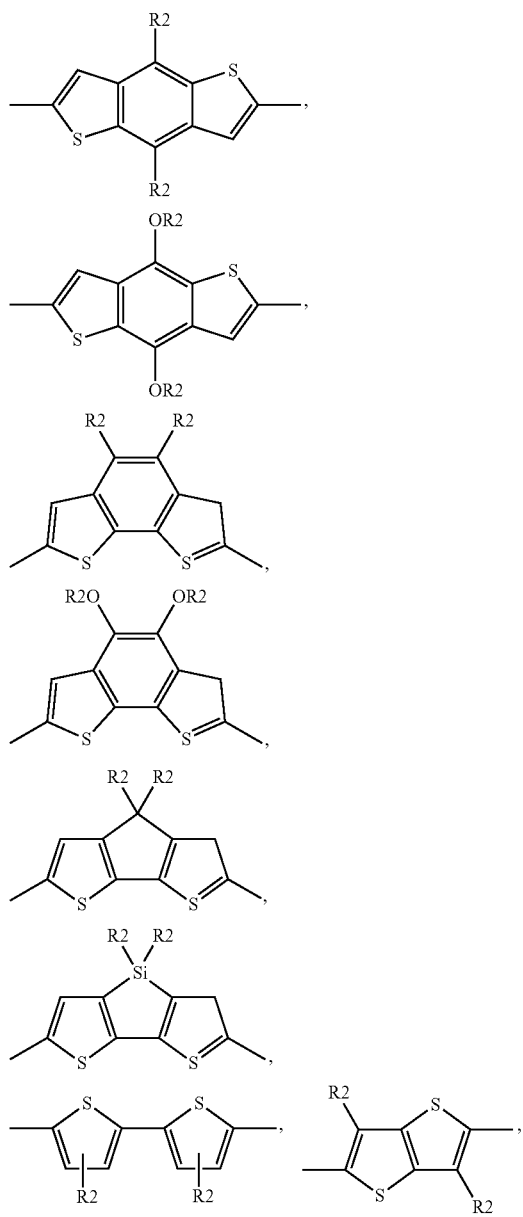

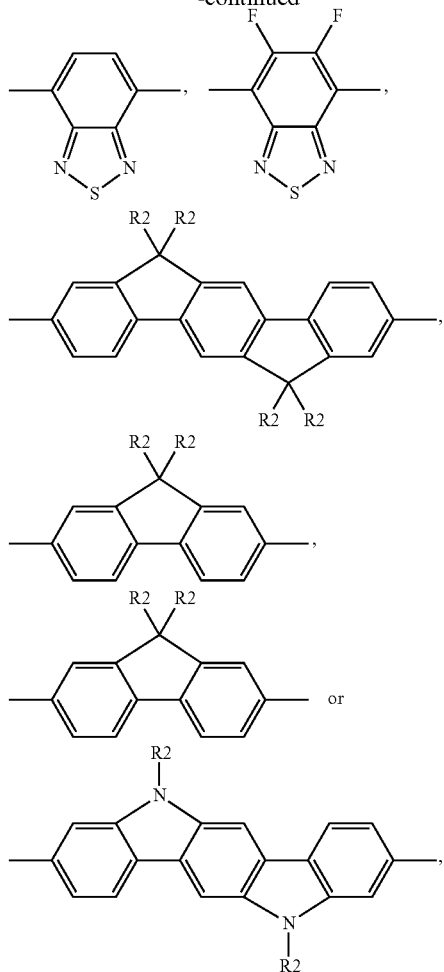

wherein R2 is a $C_1$-$C_{20}$ linear or branched alkyl group.

11. The copolymer according to claim 10, wherein each R2 is independently hexyl or 2-ethylhexyl.

12. The copolymer according to claim 1, wherein A is S, x is 1 and each R1 is independently a $C_1$-$C_{20}$ linear or branched aliphatic group.

13. The copolymer according to claim 12, wherein each R1 is independently hexyl or 2-ethylhexyl.

14. The copolymer according to claim 1, which is

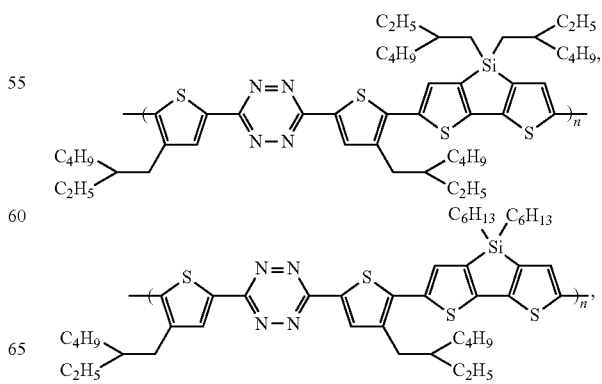

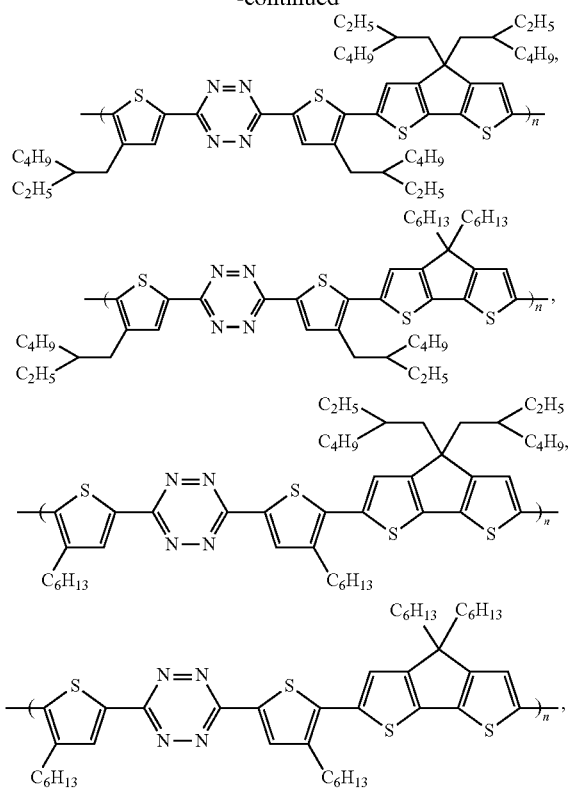

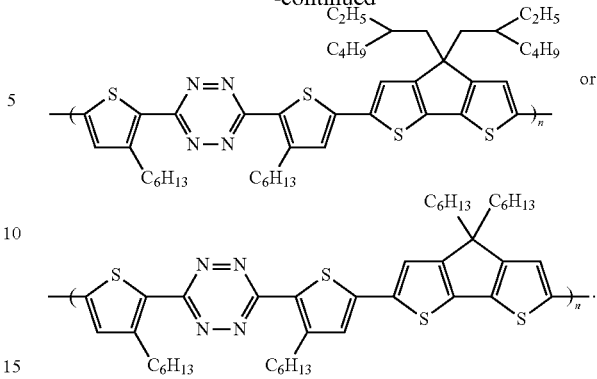

15. A film or membrane comprising a copolymer as defined in claim 1.

16. The film or membrane according to claim 15, wherein the copolymer is an electron donor and the film or membrane further comprises an electron accepting compound.

17. The film or membrane according to claim 16, wherein the electron accepting compound comprises a fullerene.

18. The film or membrane according to claim 17, wherein the fullerene comprises (6,6)-phenyl-$C_{71}$-butyric acid methyl ester.

19. The film or membrane according to claim 15 for use as an active layer for an organic electronic device.

20. The film or membrane according to claim 19, wherein the organic electronic device is a solar cell.

* * * * *